(12) United States Patent
Liu et al.

(10) Patent No.: US 7,291,765 B2
(45) Date of Patent: Nov. 6, 2007

(54) PM29 AND LEA3 PROMOTERS AND USE IN EXPRESSION OF TRANSGENIC GENES IN PLANTS

(75) Inventors: Zhan-Bin Liu, West Chester, PA (US); Johan M. Stoop, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/622,573

(22) Filed: Jan. 12, 2007

(65) Prior Publication Data

US 2007/0163005 A1    Jul. 12, 2007

Related U.S. Application Data

(62) Division of application No. 11/258,704, filed on Oct. 26, 2005, now Pat. No. 7,169,969.

(60) Provisional application No. 60/625,835, filed on Nov. 8, 2004.

(51) Int. Cl.
| | |
|---|---|
| C12N 15/82 | (2006.01) |
| C12N 5/04 | (2006.01) |
| C12N 5/10 | (2006.01) |
| A01H 5/00 | (2006.01) |
| A01H 5/10 | (2006.01) |

(52) U.S. Cl. ............ 800/278; 435/415; 435/416; 435/417; 435/412; 435/419; 435/468; 536/24.1; 800/295; 800/312; 800/287

(58) Field of Classification Search .......... None
See application file for complete search history.

(56) References Cited

U.S. PATENT DOCUMENTS

| 6,177,613 B1 | 1/2001 | Coughlan et al. |
| 2004/0158052 A1 | 8/2004 | Kinney et al. |

FOREIGN PATENT DOCUMENTS

WO    2004/071178 A2    8/2004

OTHER PUBLICATIONS

Stoop et al Published_Applications_NA_Main Database. SEQ ID No: 23 (Jun. 8, 2005, US 20060005280A1).*
K. Diane Jofuku et al., Kunitz Trypsin Inhibitor Genes are Differentially Expressed During the Soybean Life Cycle and in Transformed Tobacco Plants, the Plant Cell, vol. 1:1079-1093, 1989.
National Center for Biotechnology Information General Identifier No. 169962, Accesion No. M97285, Apr. 27, 1993, Y.-I.C. Hsing et al., Genomic Nucleotide Sequence of a Soybean Seed Maturation Protein GMPM9 Gene.

(Continued)

*Primary Examiner*—Phuong T. Bui
*Assistant Examiner*—Brendan O. Baggot

(57) ABSTRACT

The promoters of a soybean seed maturation protein PM29 and a soybean late-embryogenesis abundant protein LEA3 and fragments thereof and their use in promoting the expression of one or more heterologous nucleic acid fragments in plants are described.

7 Claims, 12 Drawing Sheets

OTHER PUBLICATIONS

National Center for Biotechnology Information General Identifier No. 4102691, Accesion No. AF004810, Apr. 14, 2005, M.D. Shih et al., Gene Cloning and Characterization of a Soybean (Glycine Max L.) Lea Protein, GMPM16.

National Center for Biotechnology Information General Identifier No. 4836406, Accession No. AF117725, May 17, 1999, Y.-I.C. Hsing et al., Characterization of a Soybean Seed Maturation Protein GMPM29.

Richard A. Jefferson, Assaying Chimeric Genes in Plants: the Gus Gene Fusion System, Plant Molecular Biology Reporter, vol. 5(4):387-405, 1987.

Pei-Fang Lee et al., Genomic Nucleotide Sequence of a Soybean Seed Maturation Protein GMPM9 Gene, Plant Physiol., vol. 100:2121-2122, 1992.

Zhang-Liang Chen et al., Regulated Expression of Genes Encoding Soybean Beta-Conglycinins in Transgenic Plants, Developmental Genetics, vol. 10:112-122, 1989.

Niels C. Nielsen et al., Characterization of the Glycinin Gene Family in Soybean, The Plant Cell, vol. 1:313-328, 1989.

* cited by examiner

SEQUENCE LISTING

```
<160> NUMBER OF SEQ ID NOS: 41

<210> SEQ ID NO 1
<211> LENGTH: 597
<212> TYPE: DNA
<213> ORGANISM: Glycine max

<400> SEQUENCE: 1
agagttttta taagttattt tatacatgaa ttaatttaa cttgtgaaaa aaattatttt      60
cttcttataa gtatttatga caaagcttat ataaacatag tcttaatttc actcagaaaa    120
acagaggagg aaaacttgtt gtatgaagcc cggctatttc atccattatc catatttgga    180
tcgaaaagag aaggaaagtg tcattttata tgtgtataaa aagtatttca tccataagta    240
atgataagat aattgtgtat gtaacattat taatgtattt aaattaaaat cataaattat    300
tttaaacaat tcttattcgt tagtgacacg ataacggata agctaataat atatctatgg    360
ttttctgtga acgtggcagc atattgatgg gaatagctct gcatgttgaa caagtggcac    420
ggtacctagc gtgccttgct cttcttttgt ctaggcttgg tttggttcgc atcttccttc    480
```

```
tcatataaat cctccaccac gtcgagtttt ctgttcaaat taaatcgttc aacactggaa    540
ctctttgata taatatagaa agagacagag agagagagac agacaagaag aacaagg       597

<210> SEQ ID NO 2
<211> LENGTH: 400
<212> TYPE: DNA
<213> ORGANISM: Glycine max

<400> SEQUENCE: 2
atcagataaa agatatgaga acattagtta gttaatagtg atagaaacta aaactaatct    60
gataagataa ttgtgtaaga ttattgatgt atttaaatta aaatcataaa ttgttttaaa   120
aaattcttat tcgttagtgc tacggtaacg gataagttat aataataata atctaattat   180
atctctggtt ttctgtgaac gtggcaacat gttgatggga aaagctctgc atgttgaaca   240
agtgcacggt acctagcgtg ccatgctctt cttttttgtc gtggcatggt ttggctcgca   300
tcttccttct cttataaaat ctccaccacg tccagttttc tgttcaaatc gttttgatat   360
atgatataga aagagagaga agaagaaaag aagaacaagg                         400

<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3
tcttctgttc ttgccgttgc tttctc                                         26

<210> SEQ ID NO 4
<211> LENGTH: 33
<212> TYPE: DNA
<213> ORGANISM: Artificial
<220> FEATURE:
<223> OTHER INFORMATION: primer

<400> SEQUENCE: 4
cgcggatccg acttgctcct tggcagcact ggt                                 33

<210> SEQ ID NO 5
<211> LENGTH: 26
<212> TYPE: DNA
<213> ORGANISM: Artificial
<220> FEATURE:
<223> OTHER INFORMATION: primer

<400> SEQUENCE: 5
tcttctgttc ttgccgttgc tttctc                                         26

<210> SEQ ID NO 6
<211> LENGTH: 34
<212> TYPE: DNA
<213> ORGANISM: Artificial
<220> FEATURE:
<223> OTHER INFORMATION: primer

<400> SEQUENCE: 6
cgcggatccc gacttgttcc ttggcagcac ttgc                                34

<210> SEQ ID NO 7
<211> LENGTH: 42
<212> TYPE: DNA
<213> ORGANISM: Artificial
```

```
<220> FEATURE:
<223> OTHER INFORMATION: primer

<400> SEQUENCE: 7
cgcggatcca gagtttttat aagttatttt atacatgaat ta                        42

<210> SEQ ID NO 8
<211> LENGTH: 39
<212> TYPE: DNA
<213> ORGANISM: Artificial
<220> FEATURE:
<223> OTHER INFORMATION: primer

<400> SEQUENCE: 8
ccttgaccat ggttgttctt cttgtctgtc tctctctct                            39

<210> SEQ ID NO 9
<211> LENGTH: 40
<212> TYPE: DNA
<213> ORGANISM: Artificial
<220> FEATURE:
<223> OTHER INFORMATION: primer

<400> SEQUENCE: 9
cgcggatcca tcagataaaa gatatgagaa cattagttag                           40

<210> SEQ ID NO 10
<211> LENGTH: 41
<212> TYPE: DNA
<213> ORGANISM: Artificial
<220> FEATURE:
<223> OTHER INFORMATION: primer

<400> SEQUENCE: 10
ccttgaccat ggttgttctt cttttcttct tctctctctt t                         41

<210> SEQ ID NO 11
<211> LENGTH: 405
<212> TYPE: DNA
<213> ORGANISM: Glycine max

<400> SEQUENCE: 11
ggaaagtgtc attttatatg tgtataaaaa gtatttcatc cataagtaat gataagataa     60
ttgtgtatgt aacattatta atgtatttaa attaaaatca taaattattt taaacaattc    120
ttattcgtta gtgacacgat aacggataag ctaataatat atctatggtt ttctgtgaac    180
gtggcagcat attgatggga atagctctgc atgttgaaca agtggcacgg tacctagcgt    240
gccttgctct tcttttgtct aggcttggtt tggttcgcat cttccttctc atataaatcc    300
tccaccacgt cgagttttct gttcaaatta aatcgttcaa cactggaact ctttgatata    360
atatagaaag agacagagag agagagacag acaagaagaa caagg                    405

<210> SEQ ID NO 12
<211> LENGTH: 182
<212> TYPE: DNA
<213> ORGANISM: Glycine max

<400> SEQUENCE: 12
ggcacggtac ctagcgtgcc ttgctcttct tttgtctagg cttggtttgg ttcgcatctt     60
ccttctcata taaatcctcc accacgtcga gttttctgtt caaattaaat cgttcaacac    120
```

```
tggaactctt tgatataata tagaaagaga cagagagaga gagacagaca agaagaacaa      180
gg                                                                    182

<210> SEQ ID NO 13
<211> LENGTH: 206
<212> TYPE: DNA
<213> ORGANISM: Glycine max

<400> SEQUENCE: 13
gtgaacgtgg caacatgttg atgggaaaag ctctgcatgt tgaacaagtg cacggtacct      60
agcgtgccat gctcttcttt tttgtcgtgg catggtttgg ctcgcatctt ccttctctta     120
taaaatctcc accacgtcca gttttctgtt caaatcgttt tgatatatga tatagaaaga    180
gagagaagaa gaaaagaaga acaagg                                          206

<210> SEQ ID NO 14
<211> LENGTH: 108
<212> TYPE: DNA
<213> ORGANISM: Glycine max

<400> SEQUENCE: 14
ggctcgcatc ttccttctct tataaaatct ccaccacgtc cagttttctg ttcaaatcgt      60
tttgatatat gatatagaaa gagagagaag aagaaaagaa gaacaagg                  108

<210> SEQ ID NO 15
<211> LENGTH: 10
<212> TYPE: DNA
<213> ORGANISM: Glycine max

<400> SEQUENCE: 15
gtgacacgat                                                             10

<210> SEQ ID NO 16
<211> LENGTH: 10
<212> TYPE: DNA
<213> ORGANISM: Glycine max

<400> SEQUENCE: 16
tcaacactgg                                                             10

<210> SEQ ID NO 17
<211> LENGTH: 10
<212> TYPE: DNA
<213> ORGANISM: Glycine max

<400> SEQUENCE: 17
aaagtgtcat                                                             10

<210> SEQ ID NO 18
<211> LENGTH: 10
<212> TYPE: DNA
<213> ORGANISM: Glycine max

<400> SEQUENCE: 18
tatgtgtata                                                             10

<210> SEQ ID NO 19
<211> LENGTH: 10
<212> TYPE: DNA
<213> ORGANISM: Glycine max
```

```
<400> SEQUENCE: 19
attgtgtatg                                                                10

<210> SEQ ID NO 20
<211> LENGTH: 10
<212> TYPE: DNA
<213> ORGANISM: Glycine max

<400> SEQUENCE: 20
tgaacgtggc                                                                10

<210> SEQ ID NO 21
<211> LENGTH: 10
<212> TYPE: DNA
<213> ORGANISM: Glycine max

<400> SEQUENCE: 21
attgtgtaag                                                                10

<210> SEQ ID NO 22
<211> LENGTH: 1406
<212> TYPE: DNA
<213> ORGANISM: Glycine max

<400> SEQUENCE: 22
gtttgttttc aaagtgtgtt ttgtttccca atcctactc ttgtgaccac aacccttcct          60
cctctttctt ttgaaacctc tttttttcta ttccccaacc aaacaagcaa acgctactca        120
ctcatcatca ctgagatcat ggctcctaat atcaccactg tcaaaccac catcaccgac         180 gctcaagcca aggtcgccac cgatcatggt cgtgcctacg tcaccttcct cgccggaaac       240
ggtgactatg tgaaggtgt cgttggcttg caaaaggtc tgagaaaagt gaagagcatg         300 tacctctgg tggttgcagt gctacccgat gttcccaag atcaccgcaa cattctcacc         360
tcccaaggtt gcattgttag agagattgag cccgtgtacc ccccagagaa tcaaacccag       420
tttgccatgg catattacgt catcaactat tccaagctac gtatttggga gtttgtggag      480
tacagcaaga tgatatacct agacggtgat atccaagttt ttgacaacat tgaccacttg       540
tttgacttgc ctgataacta cttctatgcg gtgatggact gtttctgtga gccaacttgg       600
ggccacacta acaatatca gatcggttac tgccagcagt gcccccataa ggttcagtgg       660
cccactcact ttgggcccaa acctcctctc tatttcaatg ctggcatgtt tgtgtatgag      720
cccaatttgg ctacttaccg tgacctcctt caaacagtcc aagtcaccca gcccacttcc      780
tttgctgaac aggattttttt gaacatgtac ttcaaggaca aatataggcc aattcctaat    840
gtctacaatc ttgtgctggc catgctgtgg cgtcaccctg agaacgttga gcttgacaaa    900
gttaaagtgg ttcactactg tgctgctggg tctaagcctt ggaggtacac tgggaaggag      960
gagaatatgg agagagaaga tatcaagatg ttagtgaaaa agtggtggga tatatatgag     1020
gatgagactt tggactacaa caatccactc aatgtggata agttcactgc ggcacttatg    1080
gaggttggtg aagtcaagtt cgtccgtgcc ccatctgctg cttaagagtg tctttggaaa   1140
tcaagtgtga tccaagtaca tgtacaaagt catacatcat tacattaact tttatgtatt    1200
tctaaaagtc atacatcatt acattaagtt ttatgtattt ctaaagtctt aagacttaag    1260
aggacctttt ttatkkkkcc cgcttttctt tttttctttt tccaattctg tcattgtaaa    1320
gsrgagaata ccgtatcctt aatttttataa atggatatga atttttatttg tactaaaggg   1380 ggggccggta ccaattcgcc tatagt                                          1406
```

```
<210> SEQ ID NO 23
<211> LENGTH: 1350
<212> TYPE: DNA
<213> ORGANISM: Glycine max

<400> SEQUENCE: 23
gcacgagaaa caaccaacct cttcagtgat ctttgattag tactaagcta aaccatttct      60
tattccctca aaatcaaaac cttttctttt ctagctattt cccttttcaa atcatgccac     120
ctaacatcac caccgttgtt gccaatgtca ccaccgagca attacccaag gctcgtggag     180
gaagtgggcg tgccttcgtg acctttcttg ctgggaacgg tgattacgta aagggtgtcg     240
tgggtttggc caaaggactg agaaaggcca aagcatgta cccctttggtg gttgctgtgt     300
taccagatgt tcctgaagaa catcgtgaga ttctcaaatc ccaaggttgc attgtcaggg     360
agattgaacc tgtgtaccct cctgagaacc agacccagtt cgccatggcc tattatgtca     420
tcaattactc caagctacgt atttgggagt cgtggagta caagaagacg atatacctag     480
acggtgacat ccaagtattt ggaaacatag accacttgtt tgatctgcct gataattatt     540
tctatgcggt gatggattgt ttctgcgaga agacttggag ccacccccct cagttccaga     600
ttgggtactg ccaacagtgc cctgataagg ttcaatggcc ctctcacttt ggttccaaac     660
ctcctctata tttcaatgct ggcatgtttg tttatgagcc taatctcgac acctaccgtg     720
atcttctcca aactgtccaa ctcaccaagc ccacttcttt tgctgagcag actttctca     780
acatgtactt caaggacaag tacaagccaa taccgaacat gtacaacctt gtgctggcca     840
tgttgtggcg tcaccctgaa aatgttgaac ttgataaagt tcaagtggtt cattactgtg     900
ctgctgggtc taagccttgg aggttcactg ggaaggaaga gaacatggat agggaagata    960
tcaagatgct tgtgaagaag tggtgggaca tatatgaaga tgagacactg gactacaata   1020
acaactctgt caacgtggaa cgtttcacat cggcactatt ggatgctggg ggctttcagt   1080
ttgtgccagc accttctgct gcctaatatg cttattattt acagctacaa attaatgtta   1140
attaacgaca agtatatgt attgttattt gcttttttc gtttttgggt cttatatatg     1200
aaggaacaac gtctatggtt ttaatttgga tgaccttctt gtatacaaag ccacatgtga   1260
tctcatacag cttttgatta ttattaagaa attagaggac cttttattat gagtcccttta  1320
cttaaaaaaa aaaaaaaaaa aaaaaaaaaa                                    1350

<210> SEQ ID NO 24
<211> LENGTH: 1151
<212> TYPE: DNA
<213> ORGANISM: Glycine max

<400> SEQUENCE: 24
ctaagctctc ttttagtctt actcacaaac acttttttca ctgcttccat tacgaacata      60
tatttattat atggctcctg aacttgtccc caccgttgtg aaatccagtg ctgcgttcac     120
gaaacccgcg acccttccaa ggcgtgccta cgtgacattc ctcgccggaa acggtgacta     180
cgtgaaaggg gtggttggcc tcgccaaagg gttgcgaaag gtgaaaaccg cgtacccgtt     240
ggtggtggct gtcctccccg atgtgccgga ggagcaccgt aagatcctgg agtctcaggg     300
ctgcatcgtt cgcgagatcg aacccgttta cccaccccgaa aaccaaaccc agtttgccat     360
ggcttattac gtcatcaact actccaagct ccgtatatgg gagtttgtgg agtacagcaa     420
gatgatatac ttggacggag acattgaggt atatgagaac atagaccacc tatttgacct     480
acctgatggt aactttttacg ctgtgatgga ttgtttctgc gagaagacat ggagtcacac     540
```

```
ccctcagtac aaggtgggtt actgccagca atgcccggag aaggtgcggt ggcccaccga      600
attgggtcag ccccttctc tttacttcaa cgctggcatg ttcgtgttcg aacccaacat       660
cgccacctat catgacctat tgaaaacggt gcaagtcacc actcccacct cgttcgctga      720
acaagatttc ttgaacatgt acttcaagga catttacaag ccaatccctt taaattacaa      780
tcttgtcctc gccatgctgt ggcgccaccc ggaaaacgtt aaattagacc aagtcaaggt      840
tgttcactat tgcgcagcgg ggtccaagcc atggagatat acggggaagg aagagaatat      900
gcagagggag gacataaaga tgctggtgaa gaaatggtgg gatatctaca atgatgcttc      960
gcttgactac aagccattga tgaatgcaag tgaagctcca gcagcggatg tgttgacat      1020 tgaacaattc gtgcaggctc tatcagaggt tggtcatgtt caatatgtca ccgcgccttc     1080
agcagcttaa ttaagagggc acattcaaat cacgacaaaa aacaaccaag tgaaaaaaaa     1140
aaaaaaaaaa a                                                          1151
```

<210> SEQ ID NO 25
<211> LENGTH: 36
<212> TYPE: DNA
<213> ORGANISM: Artificial
<220> FEATURE:
<223> OTHER INFORMATION: primer

<400> SEQUENCE: 25

```
aagcttgcgg ccgcgtcatc aactattcca agctac                                36
```

<210> SEQ ID NO 26
<211> LENGTH: 36
<212> TYPE: DNA
<213> ORGANISM: Artificial
<220> FEATURE:
<223> OTHER INFORMATION: primer

<400> SEQUENCE: 26

```
aagcttctcg agtcacttcc cagtgtacct ccaagg                                36
```

<210> SEQ ID NO 27
<211> LENGTH: 518
<212> TYPE: DNA
<213> ORGANISM: Glycine max

<400> SEQUENCE: 27

```
tcatcaacta ttccaagcta cgtatttggg agtttgtgga gtacagcaag atgatatacc      60
tagacggtga tatccaagtt tttgacaaca ttgaccactt gtttgacttg cctgataact     120
acttctatgc ggtgatggac tgtttctgtg agccaacttg gggccacact aaacaatatc     180
agatcggtta ctgccagcag tgcccccata aggttcagtg gccccactcac tttgggccca    240 aacctcctct ctatttcaat gctggcatgt ttgtgtatga gcccaatttg gctacttacc     300
gtgacctcct tcaaacagtc caagtcaccc agcccacttc ctttgctgaa caggatttt     360 tgaacatgta cttcaaggac aaatataggc caattcctaa tgtctacaat cttgtgctgg    420
ccatgctgtg gcgtcaccct gagaacgttg agcttgacaa agttaaagtg gttcactact    480
gtgctgctgg gtctaagcct tggaggtaca ctgggaag                             518
```

<210> SEQ ID NO 28
<211> LENGTH: 34
<212> TYPE: DNA
<213> ORGANISM: Artificial
<220> FEATURE:
<223> OTHER INFORMATION: primer

```
<400> SEQUENCE: 28
aagcttctcg aggtcatcaa ttactccaag ctac                                34

<210> SEQ ID NO 29
<211> LENGTH: 44
<212> TYPE: DNA
<213> ORGANISM: Artificial
<220> FEATURE:
<223> OTHER INFORMATION: primer

<400> SEQUENCE: 29
aagcttgcgg ccgcctgcag ttacttccca gtgaacctcc aagg                     44

<210> SEQ ID NO 30
<211> LENGTH: 519
<212> TYPE: DNA
<213> ORGANISM: Glycine max

<400> SEQUENCE: 30
gtcatcaatt actccaagct acgtatttgg gagttcgtgg agtacaagaa gacgatatac    60
ctagacggtg acatccaagt atttggaaac atagaccact tgtttgatct gcctgataat   120
tatttctatg cggtgatgga ttgtttctgc gagaagactt ggagccacac ccctcagttc   180
cagattgggt actgccaaca gtgccctgat aaggttcaat ggccctctca ctttggttcc   240
aaacctcctc tatatttcaa tgctggcatg tttgtttatg agcctaatct cgacacctac   300
cgtgatcttc tccaaactgt ccaactcacc aagcccactt cttttgctga gcaggacttt   360
ctcaacatgt acttcaagga caagtacaag ccaataccga acatgtacaa ccttgtgctg   420
gccatgttgt ggcgtcaccc tgaaaatgtt gaacttgata agttcaagt ggttcattac    480 tgtgctgctg ggtctaagcc ttggaggttc actgggaag                          519

<210> SEQ ID NO 31
<211> LENGTH: 42
<212> TYPE: DNA
<213> ORGANISM: Artificial
<220> FEATURE:
<223> OTHER INFORMATION: primer

<400> SEQUENCE: 31
aagcttgcgg ccgcctgcag gtcatcaact actccaagct cc                       42

<210> SEQ ID NO 32
<211> LENGTH: 37
<212> TYPE: DNA
<213> ORGANISM: Artificial
<220> FEATURE:
<223> OTHER INFORMATION: primer

<400> SEQUENCE: 32
aagcttgcgg ccgctacttc cccgtatatc tccatgg                             37

<210> SEQ ID NO 33
<211> LENGTH: 519
<212> TYPE: DNA
<213> ORGANISM: Glycine max

<400> SEQUENCE: 33
gtcatcaact actccaagct ccgtatatgg gagtttgtgg agtacagcaa gatgatatac    60
ttggacggag acattgaggt atatgagaac atagaccacc tatttgacct acctgatggt   120 aactttacg ctgtgatgga ttgtttctgc gagaagacat ggagtcacac ccctcagtac    180
```

```
aaggtgggtt actgccagca atgcccggag aaggtgcggt ggcccaccga attgggtcag    240
cccccttctc tttacttcaa cgctggcatg ttcgtgttcg aacccaacat cgccacctat    300
catgacctat tgaaaacggt gcaagtcacc actcccacct cgttcgctga acaagatttc    360
ttgaacatgt acttcaagga catttacaag ccaatcccct taaattacaa tcttgtcctc    420
gccatgctgt ggcgccaccc ggaaaacgtt aaattagacc aagtcaaggt tgttcactat    480
tgcgcagcgg ggtccaagcc atggagatat acggggaag                          519

<210> SEQ ID NO 34
<211> LENGTH: 81
<212> TYPE: DNA
<213> ORGANISM: Artificial
<220> FEATURE:
<223> OTHER INFORMATION: linker

<400> SEQUENCE: 34
cggccggagc tggtcatctc gctcatcgtc gagtcggcgg ccggagctgg tcatctcgct    60
catcgtcgag tcggcggccg c                                              81

<210> SEQ ID NO 35
<211> LENGTH: 69
<212> TYPE: DNA
<213> ORGANISM: Artificial
<220> FEATURE:
<223> OTHER INFORMATION: a truncated ELEL sequence

<400> SEQUENCE: 35
gcggccgccg actcgacgat gagcgagatg accagctccg gccgccgact cgacgatgag    60
cgagagctc                                                            69

<210> SEQ ID NO 36
<211> LENGTH: 67
<212> TYPE: DNA
<213> ORGANISM: Artificial
<220> FEATURE:
<223> OTHER INFORMATION: a truncated ELEL sequence

<400> SEQUENCE: 36
cggccggagc tggtcatctc gctcatcgtc gagtcggcgg ccggagctgg tcatcttcgg    60
cggccgc                                                              67

<210> SEQ ID NO 37
<211> LENGTH: 39
<212> TYPE: DNA
<213> ORGANISM: Artificial
<220> FEATURE:
<223> OTHER INFORMATION: primer

<400> SEQUENCE: 37
aagcttgcgg ccgctaagtc atcaactatt ccaagctac                           39

<210> SEQ ID NO 38
<211> LENGTH: 519
<212> TYPE: DNA
<213> ORGANISM: Glycine max

<400> SEQUENCE: 38
gtcatcaact attccaagct acgtatttgg gagtttgtgg agtacagcaa gatgatatac    60
ctagacggtg atatccaagt ttttgacaac attgaccact gtttgactt gcctgataac    120 tacttctatg cggtgatgga ctgtttctgt gagccaactt ggggccacac taaacaatat    180
```

| | |
|---|---|
| cagatcggtt actgccagca gtgcccccat aaggttcagt ggcccactca ctttgggccc | 240 |
| aaacctcctc tctatttcaa tgctggcatg tttgtgtatg agcccaattt ggctacttac | 300 |
| cgtgacctcc ttcaaacagt ccaagtcacc cagcccactt cctttgctga acaggatttt | 360 |
| ttgaacatgt acttcaagga caaatatagg ccaattccta atgtctacaa tcttgtgctg | 420 |
| gccatgctgt ggcgtcaccc tgagaacgtt gagcttgaca agttaaagt ggttcactac | 480 |
| tgtgctgctg ggtctaagcc ttggaggtac actgggaag | 519 |

<210> SEQ ID NO 39
<211> LENGTH: 81
<212> TYPE: DNA
<213> ORGANISM: Artificial
<220> FEATURE:
<223> OTHER INFORMATION: linker

<400> SEQUENCE: 39

| | |
|---|---|
| gcggccgccg actcgacgat gagcgagatg accagctccg ccgccgact cgacgatgag | 60 |
| cgagatgacc agctccggcc g | 81 |

<210> SEQ ID NO 40
<211> LENGTH: 8810
<212> TYPE: DNA
<213> ORGANISM: Artificial
<220> FEATURE:
<223> OTHER INFORMATION: plasmid SH50

<400> SEQUENCE: 40

| | |
|---|---|
| ggccgccgac tcgacgatga gcgagatgac cagctccggc cgccgactcg acgatgagcg | 60 |
| agagctccgg ccgcaagtat gaactaaaat gcacgtaggt gtaagagctc atggagagca | 120 |
| tggaatattg tatccgacca gtaacagta taataactga gctccatctc acttcttcta | 180 |
| tgaataaaca aaggatgtta tgatatatta acactctatc tatgcacctt attgttctat | 240 |
| gataaatttc ctcttattat tataaatcat ctgaatcgtg acggcttatg gaatgcttca | 300 |
| aatagtacaa aaacaaatgt gtactataag actttctaaa caattctaac tttagcattg | 360 |
| tgaacgagac ataagtgtta agaagacata acaattataa tggaagaagt tgtctccat | 420 |
| ttatatatta tatattaccc acttatgtat tatattagga tgttaaggag acataacaat | 480 |
| tataaagaga gaagtttgta tccatttata tattatatac tacccattta tatattatac | 540 |
| ttatccactt atttaatgtc tttataaggt ttgatccatg atatttctaa tattttagtt | 600 |
| gatatgtata tgaaagggta ctatttgaac tctcttactc tgtataaagg ttggatcatc | 660 |
| cttaaagtgg gtctatttaa ttttattgct tcttacagat aaaaaaaaaa ttatgagttg | 720 |
| gtttgataaa atattgaagg atttaaaata ataaaaata acatataata tatgtatata | 780 |
| aattattat aatataacat ttatctataa aaaagtaaat attgtcataa atctatacaa | 840 |
| tcgtttagcc ttgctggacg aatctcaatt atttaaacga gagtaaacat atttgacttt | 900 |
| ttggttattt aacaaattat tatttaacac tatatgaaat ttttttttt atcagcaaag | 960 |
| aataaaatta aattaaggag gacaatggtg tcccaatcct tatacaacca acttccacaa | 1020 |
| gaaagtcaag tcagagacaa caaaaaaaca agcaaaggaa attttttaat ttgagttgtc | 1080 |
| ttgtttgctg cataatttat gcagtaaaac actacacata acccttttag cagtaaagca | 1140 |
| atggttgacc gtgtgcttag cttctttat tttattttt tatcagcaaa gaataaataa | 1200 |
| aataaaatga gacacttcag ggatgtttca acgatccaa gcttggcgcg ccgttctata | 1260 |
| gtgtcaccta atcgtatgt gtatgataca taaggttatg tattaattgt agccgcgttc | 1320 |

```
taacgacaat atgtccatat ggtgcactct cagtacaatc tgctctgatg ccgcatagtt    1380
aagccagccc cgacacccgc caacacccgc tgacgcgccc tgacgggctt gtctgctccc    1440
ggcatccgct tacagacaag ctgtgaccgt ctccgggagc tgcatgtgtc agaggttttc    1500
accgtcatca ccgaaacgcg cgagacgaaa gggcctcgtg atacgcctat tttataggt    1560 taatgtcatg accaaaatcc cttaacgtga gttttcgttc cactgagcgt cagaccccgt    1620
agaaaagatc aaaggatctt cttgagatcc ttttttcctg cgcgtaatct gctgcttgca    1680
aacaaaaaaa ccaccgctac cagcggtggt ttgtttgccg gatcaagagc taccaactct    1740
ttttccgaag gtaactggct tcagcagagc gcagatacca aatactgtcc ttctagtgta    1800
gccgtagtta ggccaccact tcaagaactc tgtagcaccg cctacatacc tcgctctgct    1860
aatcctgtta ccagtggctg ctgccagtgg cgataagtcg tgtcttaccg ggttggactc    1920
aagacgatag ttaccggata aggcgcagcg gtcgggctga acgggggtt cgtgcacaca    1980 gcccagcttg gagcgaacga cctacaccga actgagatac ctacagcgtg agcattgaga    2040
aagcgccacg cttcccgaag ggagaaaggc ggacaggtat ccggtaagcg cagggtcgg    2100 aacaggagag cgcacgaggg agcttccagg gggaaacgcc tggtatcttt atagtcctgt    2160
cgggtttcgc cacctctgac ttgagcgtcg attttttgtga tgctcgtcag ggggcggag    2220 cctatggaaa aacgccagca acgcggcctt tttacggttc ctggccttt gctgccttt    2280 tgctcacatg ttctttcctg cgttatcccc tgattctgtg ataaccgta ttaccgcctt    2340 tgagtgagct gataccgctc gccgcagccg aacgaccgag cgcagcgagt cagtgagcga    2400
ggaagcggaa gagcgcccaa tacgcaaacc gcctctcccc gcgcgttggc cgattcatta    2460
atgcaggttg atcagattcg acatcgatct agtaacatag atgacaccgc gcgcgataat    2520
ttatcctagt ttgcgcgcta tattttgttt tctatcgcgt attaaatgta taattgcggg    2580
actctaatca taaaaaccca tctcataaat aacgtcatgc attacatgtt aattattaca    2640
tgcttaacgt aattcaacag aaattatatg ataatcatcg caagaccggc aacaggattc    2700
aatcttaaga aactttattg ccaaatgttt gaacgatctg cttcgacgca ctccttcttt    2760
aggtacctca ctattccttt gccctcggac gagtgctggg gcgtcggttt ccactatcgg    2820
cgagtacttc tacacagcca tcggtccaga cggccgcgct tctgcgggcg atttgtgtac    2880
gcccgacagt cccggctccg gatcggacga ttgcgtcgca tcgaccctgc gcccaagctg    2940
catcatcgaa attgccgtca accaagctct gatagagttg gtcaagacca atgcggagca    3000
tatacgcccg gagccgcggc gatcctgcaa gctccggatg cctccgctcg aagtagcgcg    3060
tctgctgctc catacaagcc aaccacggcc tccagaagaa gatgttggcg acctcgtatt    3120
gggaatcccc gaacatcgcc tcgctccagt caatgaccgc tgttatgcgg ccattgtccg    3180
tcaggacatt gttggagccg aaatccgcgt gcacgaggtg ccggacttcg ggcagtcct    3240 cggcccaaag catcagctca tcgagagcct gcgcgacgga cgcactgacg gtgtcgtcca    3300
tcacagtttg ccagtgatac acatggggat cagcaatcgc gcatatgaaa tcacgccatg    3360
tagtgtattg accgattcct tgcggtccga atgggccgaa cccgctcgtc tggctaagat    3420
cggccgcagc gatcgcatcc atggcctccg cgaccggctg cagaacagcg gcagttcgg    3480 tttcaggcag gtcttgcaac gtgacaccct gtgcacggcg ggagatgcaa taggtcaggc    3540
tctcgctgaa ttccccaatg tcaagcactt ccggaatcgg agcgcggcc gatgcaaagt    3600 gccgataaac ataacgatct ttgtagaaac catcggcgca gctatttacc cgcaggacat    3660
atccacgccc tcctacatcg aagctgaaag cacgagattc ttcgccctcc gagagctgca    3720
```

```
tcaggtcgga gacgctgtcg aacttttcga tcagaaactt ctcgacagac gtcgcggtga    3780
gttcaggctt tttcatggtt taataagaag agaaaagagt tcttttgtta tggctgaagt    3840
aatagagaaa tgagctcgag cgtgtcctct ccaaatgaaa tgaacttcct tatatagagg    3900
aagggtcttg cgaaggatag tgggattgtg cgtcatccct tacgtcagtg gagatgtcac    3960
atcaatccac ttgctttgaa gacgtggttg gaacgtcttc tttttccacg atgctcctcg    4020
tgggtggggg tccatctttg ggaccactgt cggcagaggc atcttgaatg atagcctttc    4080
ctttatcgca atgatggcat ttgtaggagc caccttcctt ttctactgtc ctttcgatga    4140
agtgacagat agctgggcaa tggaatccga ggaggtttcc cgaaattatc ctttgttgaa    4200
aagtctcaat agcccttttgg tcttctgaga ctgtatcttt gacatttttg gagtagacca    4260
gagtgtcgtg ctccaccatg ttgacgaaga ttttcttctt gtcattgagt cgtaaaagac    4320
tctgtatgaa ctgttcgcca gtcttcacgg cgagttctgt tagatcctcg atttgaatct    4380
tagactccat gcatggcctt agattcagta ggaactacct ttttagagac tccaatctct    4440
attacttgcc ttggtttatg aagcaagcct tgaatcgtcc atactggaat agtacttctg    4500
atcttgagaa atatgtcttt ctctgtgttc ttgatgcaat tagtcctgaa tcttttgact    4560
gcatctttaa ccttcttggg aaggtatttg atctcctgga gattgttact cgggtagatc    4620
gtcttgatga gacctgctgc gtaggcctct ctaaccatct gtgggtcagc attctttctg    4680
aaattgaaga ggctaacctt ctcattatca gtggtgaaca tagtgtcgtc accttcacct    4740
tcgaacttcc ttcctagatc gtaaagatag aggaaatcgt ccattgtaat ctccggggca    4800
aaggagatct cttttggggc tggatcactg ctgggccttt tggttcctag cgtgagccag    4860
tgggcttttt gctttggtgg gcttgttagg gccttagcaa agctcttggg cttgagttga    4920
gcttctcctt tggggatgaa gttcaacctg tctgtttgct gacttgttgt gtacgcgtca    4980
gctgctgctc ttgcctctgt aatagtggca aatttcttgt gtgcaactcc gggaacgccg    5040
tttgttgccg cctttgtaca accccagtca tcgtatatac cggcatgtgg accgttatac    5100
acaacgtagt agttgatatg agggtgttga atacccgatt ctgctctgag aggagcaact    5160
gtgctgttaa gctcagattt ttgtgggatt ggaattggat cgatctcgat cccgcgaaat    5220
taatacgact cactataggg agaccacaac ggtttccctc tagaaataat tttgtttaac    5280
tttaagaagg agatataccc atggaaaagc ctgaactcac cgcgacgtct gtcgagaagt    5340
ttctgatcga aaagttcgac agcgtctccg acctgatgca gctctcggag ggcgaagaat    5400
ctcgtgcttt cagcttcgat gtaggagggc gtggatatgt cctgcgggta aatagctgcg    5460
ccgatggttt ctacaaagat cgttatgttt atcggcactt tgcatcggcc gcgctcccga    5520
ttccggaagt gcttgacatt ggggaattca gcgagagcct gacctattgc atctcccgcc    5580
gtgcacaggg tgtcacgttg caagacctgc ctgaaaccga actgcccgct gttctgcagc    5640
cggtcgcgga ggctatggat gcgatcgctg cggccgatct tagccagacg agcgggttcg    5700
gcccattcgg accgcaagga atcggtcaat acactacatg gcgtgatttc atatgcgcga    5760
ttgctgatcc ccatgtgtat cactggcaaa ctgtgatgga cgacaccgtc agtgcgtccg    5820
tcgcgcaggc tctcgatgag ctgatgcttt gggccgagga ctgccccgaa gtccggcacc    5880
tcgtgcacgc ggatttcggc tccaacaatg tcctgacgga caatggccgc ataacagcgg    5940
tcattgactg gagcgaggcg atgttcgggg attcccaata cgaggtcgcc aacatcttct    6000
tctggaggcc gtggttggct tgtatggagc agcagacgcg ctacttcgag cggaggcatc    6060
cggagcttgc aggatcgccg cggctccggg cgtatatgct ccgcattggt cttgaccaac    6120
```

-continued

```
tctatcagag cttggttgac ggcaatttcg atgatgcagc ttgggcgcag ggtcgatgcg    6180
acgcaatcgt ccgatccgga gccgggactg tcgggcgtac acaaatcgcc cgcagaagcg    6240
cggccgtctg gaccgatggc tgtgtagaag tactcgccga tagtggaaac cgacgcccca    6300
gcactcgtcc gagggcaaag gaatagtgag gtacagcttg gatcgatccg gctgctaaca    6360
aagcccgaaa ggaagctgag ttggctgctg ccaccgctga gcaataacta gcataacccc    6420
ttggggcctc taaacgggtc ttgagggggtt ttttgctgaa aggaggaact atatccggat    6480
gatcgggcgc gccgtcgacg gtatcgataa gcttgatatc gaattcctgc agcccggggg    6540
atccagagtt tttataagtt attttataca tgaattaatt ttaacttgtg aaaaaaatta    6600
ttttcttctt ataagtattt atgacaaagc ttatataaac atagtcttaa tttcactcag    6660
aaaaacagag gaggaaaact tgttgtatga agcccggcta tttcatccat tatccatatt    6720
tggatcgaaa agagaaggaa agtgtcattt tatatgtgta taaaagtat ttcatccata    6780
agtaatgata agataattgt gtatgtaaca ttattaatgt atttaaatta aaatcataaa    6840
ttatttttaaa caattcttat tcgttagtga cacgataacg gataagctaa taatatatct    6900
atggttttct gtgaacgtgg cagcatattg atgggaatag ctctgcatgt tgaacaagtg    6960
gcacggtacc tagcgtgcct tgctcttctt ttgtctaggc ttggtttggt tcgcatcttc    7020
cttctcatat aaatcctcca ccacgtcgag ttttctgttc aaattaaatc gttcaacact    7080
ggaactcttt gatataatat agaaagagac agagagagag agacagacaa gaagaacaac    7140
catgctagag cggccggagc tggtcatctc gctcatcgtc gagtcggcgg ccggagctgg    7200
tcatctcgct catcgtcgag tcggcggccg cgtcatcaac tattccaagc tacgtatttg    7260
ggagtttgtg gagtacagca agatgatata cctagacggt gatatccaag tttttgacaa    7320
cattgaccac ttgtttgact tgcctgataa ctacttctat gcggtgatgg actgtttctg    7380
tgagccaact tggggccaca ctaaacaata tcagatcggt tactgccagc agtgccccca    7440
taaggttcag tggcccactc actttgggcc caaacctcct ctctatttca atgctggcat    7500
gtttgtgtat gagcccaatt tggctactta ccgtgacctc cttcaaacag tccaagtcac    7560
ccagcccact tcctttgctg aacaggattt tttgaacatg tacttcaagg acaaatatag    7620
gccaattcct aatgtctaca atcttgtgct ggccatgctg tggcgtcacc ctgagaacgt    7680
tgagcttgac aaagttaaag tggttcacta ctgtgctgct gggtctaagc cttggaggta    7740
cactgggaag tgactcgagg tcatcaatta ctccaagcta cgtatttggg agttcgtgga    7800
gtacaagaag acgatatacc tagacggtga catccaagta ttttggaaaca tagaccactt    7860
gtttgatctg cctgataatt atttctatgc ggtgatggat tgtttctgcg agaagacttg    7920
gagccacacc cctcagttcc agattgggta ctgccaacag tgccctgata aggttcaatg    7980
gccctctcac tttggttcca aacctcctct atatttcaat gctggcatgt ttgtttatga    8040
gcctaatctc gacacctacc gtgatcttct ccaaactgtc caactcacca gcccacttc    8100
ttttgctgag caggactttc tcaacatgta cttcaaggac aagtacaagc caataccgaa    8160
catgtacaac cttgtgctgg ccatgttgtg gcgtcaccct gaaatgttg aacttgataa    8220
agttcaagtg gttcattact gtgctgctgg gtctaagcct tggaggttca ctgggaagta    8280
actgcaggtc atcaactact ccaagctccg tatatgggga tttgtggagt acagcaagat    8340
gatatacttg gacggagaca ttgaggtata tgagaacata gaccacctat ttgacctacc    8400
tgatggtaac ttttacgctg tgatggattg tttctgcgag aagacatgga gtcacacccc    8460
tcagtacaag gtgggttact gccagcaatg cccggagaag gtgcggtggc ccaccgaatt    8520
```

-continued

| | |
|---|---|
| gggtcagccc ccttctcttt acttcaacgc tggcatgttc gtgttcgaac ccaacatcgc | 8580 |
| cacctatcat gacctattga aaacggtgca agtcaccact cccacctcgt tcgctgaaca | 8640 |
| agatttcttg aacatgtact tcaaggacat ttacaagcca atcccttaa attacaatct | 8700 |
| tgtcctcgcc atgctgtggc gccacccgga aaacgttaaa ttagaccaag tcaaggttgt | 8760 |
| tcactattgc gcagcggggt ccaagccatg gagatatacg gggaagtagc | 8810 |

<210> SEQ ID NO 41
<211> LENGTH: 8819
<212> TYPE: DNA
<213> ORGANISM: Artificial
<220> FEATURE:
<223> OTHER INFORMATION: plasmid SH58

<400> SEQUENCE: 41

| | |
|---|---|
| ggccgctaag tcatcaacta ttccaagcta cgtatttggg agtttgtgga gtacagcaag | 60 |
| atgatatacc tagacggtga tatccaagtt tttgacaaca ttgaccactt gtttgacttg | 120 |
| cctgataact acttctatgc ggtgatggac tgtttctgtg agccaacttg gggccacact | 180 |
| aaacaatatc agatcggtta ctgccagcag tgccccata aggttcagtg gcccactcac | 240 |
| tttgggccca acctcctct ctatttcaat gctggcatgt ttgtgtatga gcccaatttg | 300 |
| gctacttacc gtgacctcct tcaaacagtc caagtcaccc agcccacttc ctttgctgaa | 360 |
| caggattttt tgaacatgta cttcaaggac aaatataggc caattcctaa tgtctacaat | 420 |
| cttgtgctgg ccatgctgtg gcgtcaccct gagaacgttg agcttgacaa agttaaagtg | 480 |
| gttcactact gtgctgctgg gtctaagcct tggaggtaca ctgggaagtg actcgaggtc | 540 |
| atcaattact ccaagctacg tatttgggag ttcgtggagt acaagaagac gatataccta | 600 |
| gacggtgaca tccaagtatt tggaaacata gaccacttgt ttgatctgcc tgataattat | 660 |
| ttctatgcgg tgatggattg tttctgcgag aagacttgga gccacacccc tcagttccag | 720 |
| attgggtact gccaacagtg ccctgataag gttcaatggc cctctcactt tggttccaaa | 780 |
| cctcctctat atttcaatgc tggcatgttt gtttatgagc ctaatctcga cacctaccgt | 840 |
| gatcttctcc aaactgtcca actcaccaag cccacttctt tgctgagca ggactttctc | 900 |
| aacatgtact tcaaggacaa gtacaagcca ataccgaaca tgtacaacct tgtgctggcc | 960 |
| atgttgtggc gtcaccctga aaatgttgaa cttgataaag ttcaagtggt tcattactgt | 1020 |
| gctgctgggt ctaagccttg gaggttcact gggaagtaac tgcaggtcat caactactcc | 1080 |
| aagctccgta tatgggagtt tgtggagtac agcaagatga tatacttgga cggagacatt | 1140 |
| gaggtatatg agaacataga ccacctattt gacctacctg atggtaactt ttacgctgtg | 1200 |
| atggattgtt tctgcgagaa gacatggagt cacaccctc agtacaaggt gggttactgc | 1260 |
| cagcaatgcc cggagaaggt gcggtggccc accgaattgg gtcagccccc ttctctttac | 1320 |
| ttcaacgctg gcatgttcgt gttcgaaccc aacatcgcca cctatcatga cctattgaaa | 1380 |
| acggtgcaag tcaccactcc cacctcgttc gctgaacaag atttcttgaa catgtacttc | 1440 |
| aaggacattt acaagccaat ccctttaaat tacaatcttg tcctcgccat gctgtggcgc | 1500 |
| cacccggaaa acgttaaatt agaccaagtc aaggttgttc actattgcgc agcggggtcc | 1560 |
| aagccatgga gatatacggg gaagtagcgg ccgccgactc gacgatgagc gagatgacca | 1620 |
| gctccggccg ccgactcgac gatgagcgag atgaccagct ccggccgcaa gtatgaacta | 1680 |
| aaatgcacgt aggtgtaaga gctcatggag agcatggaat attgtatccg accatgtaac | 1740 |
| agtataataa ctgagctcca tctcacttct tctatgaata aacaaaggat gttatgatat | 1800 |

```
attaacactc tatctatgca ccttattgtt ctatgataaa tttcctctta ttattataaa    1860
tcatctgaat cgtgacggct tatggaatgc ttcaaatagt acaaaaacaa atgtgtacta    1920
taagactttc taaacaattc taactttagc attgtgaacg agacataagt gttaagaaga    1980
cataacaatt ataatggaag aagtttgtct ccatttatat attatatatt acccacttat    2040
gtattatatt aggatgttaa ggagacataa caattataaa gagagaagtt tgtatccatt    2100
tatatattat atactaccca tttatatatt atacttatcc acttatttaa tgtctttata    2160
aggtttgatc catgatattt ctaatatttt agttgatatg tatatgaaag ggtactattt    2220
gaactctctt actctgtata aaggttggat catcctaaaa gtgggtctat ttaattttat    2280
tgcttcttac agataaaaaa aaaattatga gttggtttga taaaatattg aaggatttaa    2340
aataataata ataacatat aatatatgta tataaattta ttataatata acatttatct    2400 ataaaaagt aaatattgtc ataaatctat acaatcgttt agccttgctg gacgaatctc     2460
aattatttaa acgagagtaa acatatttga cttttttggtt atttaacaaa ttattattta    2520
acactatatg aaatttttt tttttatcagc aaagaataaa attaaattaa ggaggacaat    2580
ggtgtcccaa tccttataca accaacttcc acaagaaagt caagtcagag acaacaaaaa    2640
aacaagcaaa ggaaatttttt taatttgagt tgtcttgttt gctgcataat ttatgcagta    2700
aaacactaca cataaccctt ttagcagtaa agcaatggtt gaccgtgtgc ttagcttctt    2760 ttatttatt tttttatcag caaagaataa ataaaataaa atgagacact tcagggatgt    2820
ttcaacggat ccaagcttgg cgcgccgttc tatagtgtca cctaaatcgt atgtgtatga    2880
tacataaggt tatgtattaa ttgtagccgc gttctaacga caatatgtcc atatggtgca    2940
ctctcagtac aatctgctct gatgccgcat agttaagcca gccccgacac ccgccaacac    3000
ccgctgacgc gccctgacgg gcttgtctgc tcccggcatc cgcttacaga caagctgtga    3060
ccgtctccgg gagctgcatg tgtcagaggt tttcaccgtc atccgaaaa cgcgcgagac     3120 gaaagggcct cgtgatacgc ctatttttat aggttaatgt catgaccaaa atcccttaac    3180
gtgagttttc gttccactga gcgtcagacc ccgtagaaaa gatcaaagga tcttcttgag    3240 atccttttttt tctgcgcgta atctgctgct tgcaaacaaa aaaaccaccg ctaccagcgg    3300
tggtttgttt gccggatcaa gagctaccaa ctctttttcc gaaggtaact ggcttcagca    3360
gagcgcagat accaaatact gtccttctag tgtagccgta gttaggccac cacttcaaga    3420
actctgtagc accgcctaca tacctcgctc tgctaatcct gttaccagtg gctgctgcca    3480
gtggcgataa gtcgtgtctt accgggttgg actcaagacg atagttaccg gataaggcgc    3540
agcggtcggg ctgaacgggg ggttcgtgca cacagcccag cttggagcga acgacctaca    3600
ccgaactgag atacctacag cgtgagcatt gagaaagcgc cacgcttccc gaagggagaa    3660
aggcggacag gtatccggta agcggcaggg tcggaacagg agagcgcacg agggagcttc    3720
cagggggaaa cgcctggtat ctttatagtc ctgtcgggtt tcgccacctc tgacttgagc    3780
gtcgattttt gtgatgctcg tcagggggc ggagcctatg gaaaaacgcc agcaacgcgg     3840 ccttttttacg gttcctggcc ttttgctggc cttttgctca catgttcttt cctgcgttat    3900
cccctgattc tgtggataac cgtattaccg cctttgagtg agctgatacc gctcgccgca    3960
gccgaacgac cgagcgcagc gagtcagtga gcgaggaagc ggaagagcgc ccaatacgca    4020
aaccgcctct ccccgcgcgt tggccgattc attaatgcag gttgatcaga ttcgacatcg    4080
atctagtaac atagatgaca ccgcgcgcga taatttatcc tagtttgcgc gctatatttt    4140
gttttctatc gcgtattaaa tgtataattg cgggactcta atcataaaaa cccatctcat    4200
```

-continued

```
aaataacgtc atgcattaca tgttaattat tacatgctta acgtaattca acagaaatta    4260
tatgataatc atcgcaagac cggcaacagg attcaatctt aagaaacttt attgccaaat    4320
gtttgaacga tctgcttcga cgcactcctt ctttaggtac ctcactattc ctttgccctc    4380
ggacgagtgc tggggcgtcg gtttccacta tcggcgagta cttctacaca gccatcggtc    4440
cagacggccg cgcttctgcg ggcgatttgt gtacgcccga cagtcccggc tccggatcgg    4500
acgattgcgt cgcatcgacc ctgcgcccaa gctgcatcat cgaaattgcc gtcaaccaag    4560
ctctgataga gttggtcaag accaatgcgg agcatatacg cccggagccg cggcgatcct    4620
gcaagctccg gatgcctccg ctcgaagtag cgcgtctgct gctccataca agccaaccac    4680
ggcctccaga agaagatgtt ggcgacctcg tattgggaat ccccgaacat cgcctcgctc    4740
cagtcaatga ccgctgttat gcggccattg tccgtcagga cattgttgga gccgaaatcc    4800
gcgtgcacga ggtgccggac ttcggggcag tcctcggccc aaagcatcag ctcatcgaga    4860
gcctgcgcga cggacgcact gacggtgtcg tccatcacag tttgccagtg atacacatgg    4920
ggatcagcaa tcgcgcatat gaaatcacgc catgtagtgt attgaccgat tccttgcggt    4980
ccgaatgggc cgaacccgct cgtctggcta agatcggccg cagcgatcgc atccatggcc    5040
tccgcgaccg gctgcagaac agcgggcagt tcggtttcag gcaggtcttg caacgtgaca    5100
ccctgtgcac ggcgggagat gcaataggtc aggctctcgc tgaattcccc aatgtcaagc    5160
acttccggaa tcgggagcgc ggccgatgca aagtgccgat aaacataacg atctttgtag    5220
aaaccatcgg cgcagctatt tacccgcagg acatatccac gccctcctac atcgaagctg    5280
aaagcacgag attcttcgcc ctccgagagc tgcatcaggt cggagacgct gtcgaacttt    5340
tcgatcagaa acttctcgac agacgtcgcg gtgagttcag gctttttcat ggtttaataa    5400
gaagagaaaa gagttctttt gttatggctg aagtaataga gaaatgagct cgagcgtgtc    5460
ctctccaaat gaaatgaact tccttatata gaggaagggt cttgcgaagg atagtgggat    5520
tgtgcgtcat cccttacgtc agtggagatg tcacatcaat ccacttgctt tgaagacgtg    5580
gttgaacgt cttcttttc cacgatgctc ctcgtgggtg gggtccatc tttgggacca    5640
ctgtcggcag aggcatcttg aatgatagcc tttcctttat cgcaatgatg gcatttgtag    5700
gagccacctt cctttctac tgtccttcg atgaagtgac agatagctgg gcaatggaat    5760
ccgaggaggt ttcccgaaat tatcctttgt tgaaaagtct caatagccct ttggtcttct    5820
gagactgtat ctttgacatt tttggagtag accagagtgt cgtgctccac catgttgacg    5880
aagattttct tcttgtcatt gagtcgtaaa agactctgta tgaactgttc gccagtcttc    5940
acggcgagtt ctgttagatc ctcgatttga atcttagact ccatgcatgg ccttagattc    6000
agtaggaact accttttag agactccaat ctctattact tgccttggtt tatgaagcaa    6060
gccttgaatc gtccatactg gaatagtact tctgatcttg agaaatatgt ctttctctgt    6120
gttcttgatg caattagtcc tgaatctttt gactgcatct ttaaccttct tgggaaggta    6180
tttgatctcc tggagattgt tactcgggta gatcgtcttg atgagacctg ctgcgtaggc    6240
ctctctaacc atcgtgggt cagcattctt tctgaaattg aagaggctaa ccttctcatt    6300
atcagtggtg aacatagtgt cgtcaccttc accttcgaac ttccttccta gatcgtaaag    6360
atagaggaaa tcgtccattg taatctccgg ggcaaaggag atctctttg gggctggatc    6420
actgctgggc cttttggttc ctagcgtgag ccagtgggct ttttgctttg gtgggcttgt    6480
tagggcctta gcaaagctct tgggcttgag ttgagcttct cctttgggga tgaagttcaa    6540
cctgtctgtt tgctgacttg ttgtgtacgc gtcagctgct gctcttgcct ctgtaatagt    6600
```

```
ggcaaatttc ttgtgtgcaa ctccgggaac gccgtttgtt gccgcctttg tacaacccca    6660
gtcatcgtat ataccggcat gtggaccgtt atacacaacg tagtagttga tatgagggtg    6720
ttgaataccc gattctgctc tgagaggagc aactgtgctg ttaagctcag attttttgtgg   6780 gattggaatt ggatcgatct cgatcccgcg aaattaatac gactcactat agggagacca    6840
caacggtttc cctctagaaa taattttgtt aactttaag aaggagatat acccatggaa     6900
aagcctgaac tcaccgcgac gtctgtcgag aagtttctga tcgaaaagtt cgacagcgtc    6960
tccgacctga tgcagctctc ggagggcgaa gaatctcgtg ctttcagctt cgatgtagga    7020
gggcgtggat atgtcctgcg ggtaaatagc tgcgccgatg gtttctacaa agatcgttat    7080
gtttatcggc actttgcatc ggccgcgctc ccgattccgg aagtgcttga cattggggaa    7140
ttcagcgaga gcctgaccta ttgcatctcc cgccgtgcac agggtgtcac gttgcaagac    7200
ctgcctgaaa ccgaactgcc cgctgttctg cagccggtcg cggaggctat ggatgcgatc    7260
gctgcggccg atcttagcca cgagcgggg ttcggcccat tcggaccgca aggaatcggt     7320
caatacacta catggcgtga tttcatatgc gcgattgctg atccccatgt gtatcactgg    7380
caaactgtga tggacgacac cgtcagtgcg tccgtcgcgc aggctctcga tgagctgatg    7440
ctttgggccg aggactgccc cgaagtccgg cacctcgtgc acgcggattt cggctccaac    7500
aatgtcctga cggacaatgg ccgcataaca gcggtcattg actggagcga ggcgatgttc    7560
ggggattccc aatacgaggt cgccaacatc ttcttctgga ggccgtggtt ggcttgtatg    7620
gagcagcaga cgcgctactt cgagcggagg catccggagc ttgcaggatc gccgcggctc    7680
cgggcgtata tgctccgcat tggtcttgac caactctatc agagcttggt tgacggcaat    7740
ttcgatgatg cagcttgggc gcagggtcga tgcgacgcaa tcgtccgatc cggagccggg    7800
actgtcgggc gtacacaaat cgcccgcaga agcgcggccg tctggaccga tggctgtgta    7860
gaagtactcg ccgatagtgg aaaccgacgc cccagcactc gtccgagggc aaaggaatag    7920
tgaggtacag cttggatcga tccggctgct aacaaagccc gaaggaagc tgagttggct     7980 gctgccaccg ctgagcaata actagcataa ccccttgggg cctctaaacg ggtcttgagg    8040
ggttttttgc tgaaaggagg aactatatcc ggatgatcgg gcgcgccgtc gacggtatcg    8100
ataagcttga tatcgaattc ctgcagcccg ggggatccag agtttttata agttatttta    8160
tacatgaatt aattttaact tgtgaaaaaa attattttct tcttataagt atttatgaca    8220
aagcttatat aaacatagtc ttaatttcac tcagaaaaac agaggaggaa aacttgttgt    8280
atgaagcccg gctatttcat ccattatcca tatttggatc gaaaagagaa ggaaagtgtc    8340
attttatatg tgtataaaaa gtatttcatc cataagtaat gataagataa ttgtgtatgt    8400
aacattatta atgtatttaa attaaaatca taaattattt taaacaattc ttattcgtta    8460
gtgacacgat aacggataag ctaataatat atctatggtt ttctgtgaac gtggcagcat    8520
attgatggga atagctctgc atgttgaaca agtggcacgg tacctagcgt gccttgctct    8580
tcttttgtct aggcttggtt tggttcgcat cttccttctc atataaatcc tccaccacgt    8640 cgagtttttct gttcaaatta aatcgttcaa cactggaact ctttgatata atatagaaag    8700
agacagagag agagagacag acaagaagaa caaccatgct agagcggccg gagctggtca    8760
tctcgctcat cgtcgagtcg gcggccggag ctggtcatct cgctcatcgt cgagtcggc    8819
```

PM29 AND LEA3 PROMOTERS AND USE IN EXPRESSION OF TRANSGENIC GENES IN PLANTS

This application claims the benefit of U.S. Provisional Application No. 60/625,835, filed Nov. 8, 2004, the entire content of which is herein incorporated by reference.

FIELD OF THE INVENTION

This invention relates to plant promoters, in particular, to PM29 and LEA3 promoters and fragments thereof and their use in altering expression of at least one heterologous nucleic acid fragment in plants.

BACKGROUND OF THE INVENTION

Recent advances in plant genetic engineering have opened new doors to engineer plants having improved characteristics or traits, such as, resistance to plant diseases, insect resistance, herbicidal resistance, enhanced stability or shelf-life of the ultimate consumer product obtained from the plants and improvement of the nutritional quality of the edible portions of the plant. Thus, a desired gene (or genes) from a source different than the plant, but engineered to impart different or improved characteristics or qualities, can be incorporated into the plant's genome. This new gene (or genes) can then be expressed in the plant cell to exhibit the desired new trait or characteristic.

It is important that the proper regulatory signals be present and be in the proper location with respect to the gene in order to obtain expression of the newly inserted gene in the plant cell. These regulatory signals include a promoter region, a 5' non-translated leader sequence and a 3' transcription termination/polyadenylation sequence.

A promoter is a short DNA sequence, usually upstream (5') to the relevant coding sequence, to which RNA polymerase binds before initiating transcription. This binding aligns the RNA polymerase so that transcription will initiate at a specific site. The nucleotide sequence of the promoter determines the nature of the enzyme that attaches to it and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cells to cause termination of the RNA and the addition of polyadenylate nucleotides to the 3' end.

It has been shown that certain promoters are able to direct RNA synthesis at a higher rate than others. These are called "strong promoters". Certain other promoters have been shown to direct RNA production at higher levels only in particular types of cells or tissues and are often referred to as "tissue specific promoters". Many seed storage protein genes' promoters have been well characterized and widely used, such as the phaseolin gene promoter of *Phaseolus vulgaris*, the helianthinin gene of sunflower, the β-conglycinin gene of soybean (Chen et al., *Dev. Genet.* 10:112-122 (1989)), the napin gene promoter of *Brassica napus* (Ellerstrom et al., *Plant Mol. Biol.* 32:1019-1027 (1996)), the oleosin gene promoters of *Brassica* and *Arabidopsis* (Keddie et al., *Plant Mol. Biol.* 24:327-340 (1994); Li, Texas A&M Ph.D. dissertation, pp.107-128 (1997); Plant et al., *Plant Mol. Biol.* 25:193-205 (1994)). Another class of tissue specific promoters is described in U.S. Pat. No. 5,589,583, issued to Klee et al. on Dec. 31, 1996; these plant promoters are capable of conferring high levels of transcription of chimeric genes in meristematic tissues and/or rapidly dividing cells. "Inducible promoters" direct RNA production in response to certain environmental factors, such as heat shock, light, hormones, ion concentrations etc. (Espartero et al., *Plant Mol. Biol.* 25:217-227 (1994); Gomez-Gomez and Carrasco, *Plant Physiol.* 117:397-405 (1998); Holtorf et al., *Plant Mol. Biol.* 29:637-646 (1995); MacDowell et al., *Plant Physiol.* 111:699-711 (1996); Mathur et al., *Biochem. Biophys. Acta* 1137:338-348 (1992); Mett et al., *Transgenic Res.* 5:105-113 (1996); Schoffl et al., *Mol. Gen. Genet.* 217:246-253 (1989); Ulmasov et al., *Plant Physiol.* 108:919-927 (1995)).

Since the patterns of expression of a chimeric gene (or genes) introduced into a plant are controlled using promoters, there is an ongoing interest in the isolation and identification of novel promoters which are capable of controlling expression of a chimeric gene or (genes). Promoters that drive expression only in the developing seeds are of particular interest. Another desirable feature of a promoter would be an expression pattern that occurs very late in development in the developing seed or at seed maturity.

SUMMARY OF THE INVENTION

This invention concerns an isolated nucleic acid fragment comprising a promoter wherein said promoter consists essentially of the nucleotide sequence set forth in SEQ ID NOs:1, 2, 11 or said promoter consists essentially of a fragment that is substantially similar and functionally equivalent to the nucleotide sequence set forth in SEQ ID NOs:1, 2 or 11.

In a second embodiment, this invention concerns a recombinant expression construct comprising at least one heterologous nucleic acid fragment operably linked to the promoter of the invention.

In a third embodiment, a cell, plant, or seed comprising a recombinant expression construct of the present invention.

In a fourth embodiment, this invention concerns plants comprising this recombinant expression construct and seeds obtained from such plants.

In a fifth embodiment, this invention concerns a method of altering (increasing or decreasing) expression of at least one heterologous nucleic acid fragment in a plant cell which comprises:

(a) transforming a plant cell with the recombinant expression construct described above;
(b) growing fertile mature plants from the transformed plant cell of step (a);
(c) selecting plants containing the transformed plant cell wherein the expression of the heterologous nucleic acid fragment is increased or decreased.

In a sixth embodiment, this invention concerns a method for reducing the level of at least one raffinose saccharide in a host cell comprising:

(a) transforming a host cell with a recombinant expression construct comprising at least one galactinol synthase nucleic acid fragment operably linked to a promoter wherein said promoter consists essentially of the nucleotide sequence set forth in SEQ ID NOs:1, 2 or 11; and
(b) growing the transformed host cell under conditions that are suitable for expression of the recombinant DNA construct, wherein expression of the recombinant DNA construct results in production of reduced levels of at least one raffinose saccharide in the transformed host cell when compared to a corresponding nontransformed host cell.

In a seventh embodiment, this invention concerns an isolated nucleic acid fragment comprising a seed-specific plant PM29, or LEA3, promoter.

BRIEF DESCRIPTION OF THE DRAWINGS AND SEQUENCES

The invention can be more fully understood from the following detailed description, the drawings and the Sequence Descriptions that form a part of this application. The sequence descriptions and Sequence Listing attached hereto comply with the rules governing nucleotide and/or amino acid sequence disclosures in patent applications as set forth in 37 C.F.R. §1.821-1.825. The Sequence Descriptions contain the three letter codes for amino acids as defined in 37 C.F.R. § 1.821-1.825, which are incorporated herein by reference.

SEQ ID NO:1 is the DNA sequence comprising a 597 nucleotide soybean PM29 promoter.

SEQ ID NO:2 is the DNA sequence comprising a 400 nucleotide soybean LEA3 promoter.

SEQ ID NO:3 is an oligonucleotide primer used in the first PCR amplification of the PM29 promoter.

SEQ ID NO:4 is an oligonucleotide primer used in the second nested PCR amplification of the PM29 promoter.

SEQ ID NO:5 is an oligonucleotide primer used in the first PCR amplification of the LEA3 promoter.

SEQ ID NO:6 is an oligonucleotide primer used in the second nested PCR amplification of the LEA3 promoter.

SEQ ID NO:7 is an oligonucleotide primer used in the PCR amplification of the PM29 promoter when paired with SEQ ID NO:8.

SEQ ID NO:8 is an oligonucleotide primer used in the PCR amplification of the PM29 promoter when paired with SEQ ID NO:7.

SEQ ID NO:9 is an oligonucleotide primer used in the PCR amplification of the LEA3 promoter when paired with SEQ ID NO:10.

SEQ ID NO:10 is an oligonucleotide primer used in the PCR amplification of the LEA3 promoter when paired with SEQ ID NO:9.

SEQ ID NO:11 is a 405 basepair truncated form of the PM29 promoter shown in SEQ ID NO:1 (bp 193-597 of SEQ ID NO:1).

SEQ ID NO:12 is a 182 basepair truncated form of the PM29 promoter shown in SEQ ID NO:1 (bp 416-597 of SEQ ID NO:1).

SEQ ID NO:13 is 206 basepair truncated form of the LEA3 promoter shown in SEQ ID NO:2 (bp 195-400 of SEQ ID NO:2).

SEQ ID NO:14 is a 108 basepair truncated form of the LEA3 promoter shown in SEQ ID NO:2 (bp 293-400 of SEQ ID NO:2).

SEQ ID NO:15 is the ACAC element GTGACACGAT of the PM29 promoter.

SEQ ID NO:16 is the ACAC element TCAACACTGG of the PM29 promoter.

SEQ ID NO:17 is the GTGT element AAAGTGTCAT of the PM29 promoter.

SEQ ID NO:18 is the GTGT element TATGTGTATA of the PM29 promoter.

SEQ ID NO:19 is the GTGT element ATTGTGTATG of the PM29 promoter.

SEQ ID NO:20 is a part (TGAACGTGGC) of the RY-G-box seed-specific coupling element (AACATGTTG, TGCATGTTG, GCCATGCTC, GGCATGGTT, TGAACGTGGC) of the PM29 and LEA3 promoter.

SEQ ID NO:21 is the GTGT element ATTGTGTAAG of the LEA3 promoter.

SEQ ID NO:22 is the nucleotide sequence of soybean seed galactinol synthase cDNA (GAS1). The nucleotide 1 is the first nucleotide following the Pst1 restriction site, reading from 5' to 3' on the cDNA insert, nucleotide 1406 is the last nucleotide of the cDNA insert, immediately before the first nucleotide of the Kpn1 restriction site of plasmid pS21. Nucleotides 1 to 138 are the 5' untranslated sequence, nucleotides 139 to 141 are the translation initiation codon, nucleotides 1123 to 1125 are the termination codon, and nucleotides 1126 to 1406 are the 3' untranslated sequence.

SEQ ID NO:23 is the nucleotide sequence of soybean seed galactinol synthase cDNA (GAS2) (found in clone ses4d.pk0017. b8).

SEQ ID NO:24 is the nucleotide sequence of soybean seed galactinol synthase cDNA (GAS3).

SEQ ID NO:25 is the GAS1 oligonucleotide primer designed to add a Not1 restriction endonuclease site at the 5' end.

SEQ ID NO:26 is the GAS1 oligonucleotide primer designed to add a stop codon (TGA) and an Xho1 restriction endonuclease site at the 3' end.

SEQ ID NO:27 is the DNA sequence comprising the 518 bp polynucleotide from soybean GAS1 resulting from the GAS1 oligonucleotides primers of SEQ ID NO:25 and SEQ ID NO:26.

SEQ ID NO:28 is the GAS2 oligonucleotide primer designed to add a Xho1 restriction endonuclease site at the 5' end.

SEQ ID NO:29 is the GAS2 oligonucleotide primer designed to add a sstop codon (TAA) and a Pst1 restriction endonuclease site at the 3' end.

SEQ ID NO:30 is the DNA sequence comprising the 519 bp polynucleotide from soybean GAS2 resulting from the GAS2 oligonucleotides primers of SEQ ID NO:28 and SEQ ID NO:29.

SEQ ID NO:31 is the GAS3 oligonucleotide primer designed to add a Pst1 restriction endonuclease site at the 5' end.

SEQ ID NO:32 is the GAS3 oligonucleotide primer designed to add a stop codon (TAG) and a Not1 restriction endonuclease site at the 3' end.

SEQ ID NO:33 is the DNA sequence comprising the 519 bp polynucleotide from soybean GAS3 resulting from the GAS3 oligonucleotides primers of SEQ ID NO:31 and SEQ ID NO:32.

SEQ ID NO:34 is the linker designated ELVISLIVES.

SEQ ID NO:35 is a truncated ELEL sequence. The truncated sequence is 1X complementary repeat and is missing the "tgacca" of the ELEL sequence shown in SEQ ID NO:34.

SEQ ID NO:36 is a truncated ELEL sequence. The truncated sequence is 1X repeat and is missing the "cgctcatcgtcgag" of the ELEL sequence shown in SEQ ID NO:34.

SEQ ID NO:37 is the GAS1 oligonucleotide primer designed to add a stop codon (TAA) a Not1 restriction endonuclease site at the 5' end.

SEQ ID NO:38 is the resulting 519 bp polynucleotide from the GAS1 oligonucleotides primers of SEQ ID NO:37 and SEQ ID NO:26.

SEQ ID NO:39 is the linker designated SEVILSIVLE (complementary strand of SEQ ID NO:34).

SEQ ID NO:40 is the 8810 bp sequence of SH50.

SEQ ID NO:41 is the 8819 bp sequence of SH58.

FIG. 1 depicts soybean PM29-GUS and soybean LEA3-GUS expression in *Arabidopsis*. The dark developing seeds are staining blue due to GUS specific expression in the seeds. This figure demonstrates that the PM29 and LEA3 promoters are capable of directing seed-specific expression of a reporter construct. Untransformed seeds are not blue and show up as pale seeds.

Figure 7:
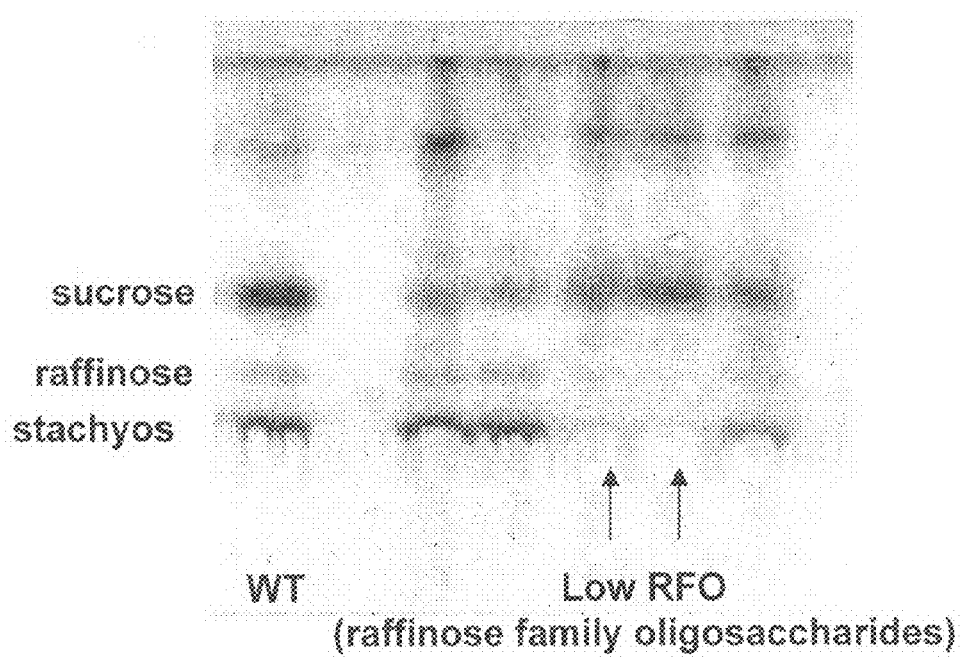

FIG. 7 is a thin layer chromatography analysis of individual somatic embryos transformed with a PM29 driven construct targeted for silencing of multiple galactinol synthase enzymes. As shown in FIG. 7, the two lines labeled PM29-GAS show reduced levels of raffinose sugars (raffinose and stachyose lowest bands) when compared to a to wild-type soybean. The arrow indicates somatic embryos with reduced raffinose family oligosaccharides. (WT=wild type control, S=sucrose, Rf=raffinose and St=stachyose standard)

Figure 8:
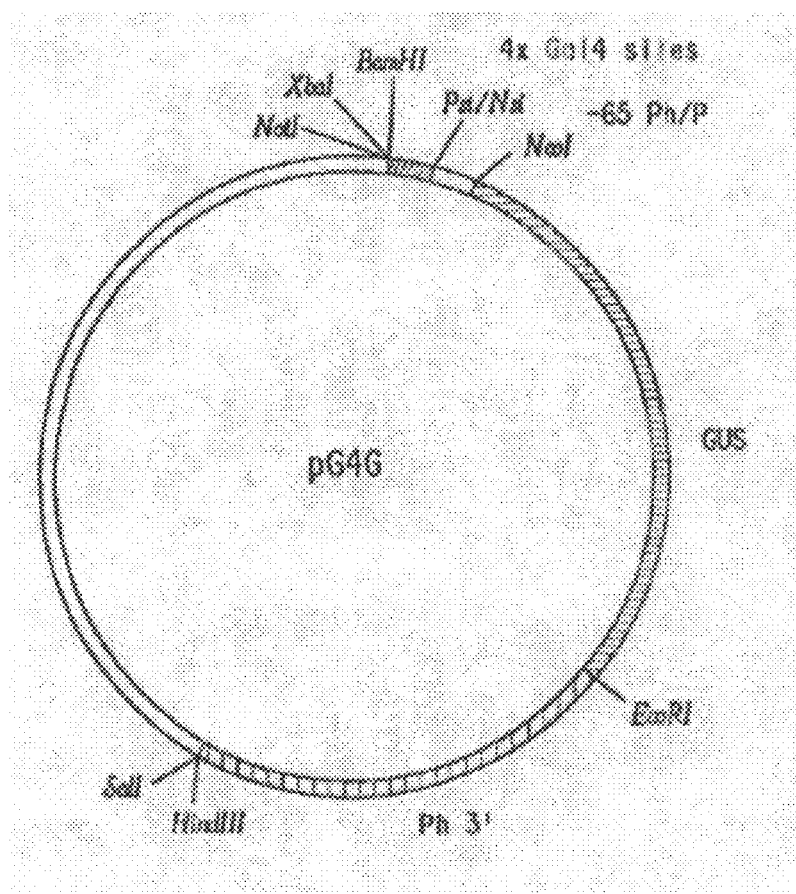

FIG. 8 is a map of plasmid pG4G which contains the chimeric G4G gene in pGEM9Zf. The G4G gene consists of 4 Gal4 binding sites, the -65 phaseolin promoter region and leader, the GUS coding region, and a phaseolin 3' polyadenylation signal sequence region.

Figure 9:
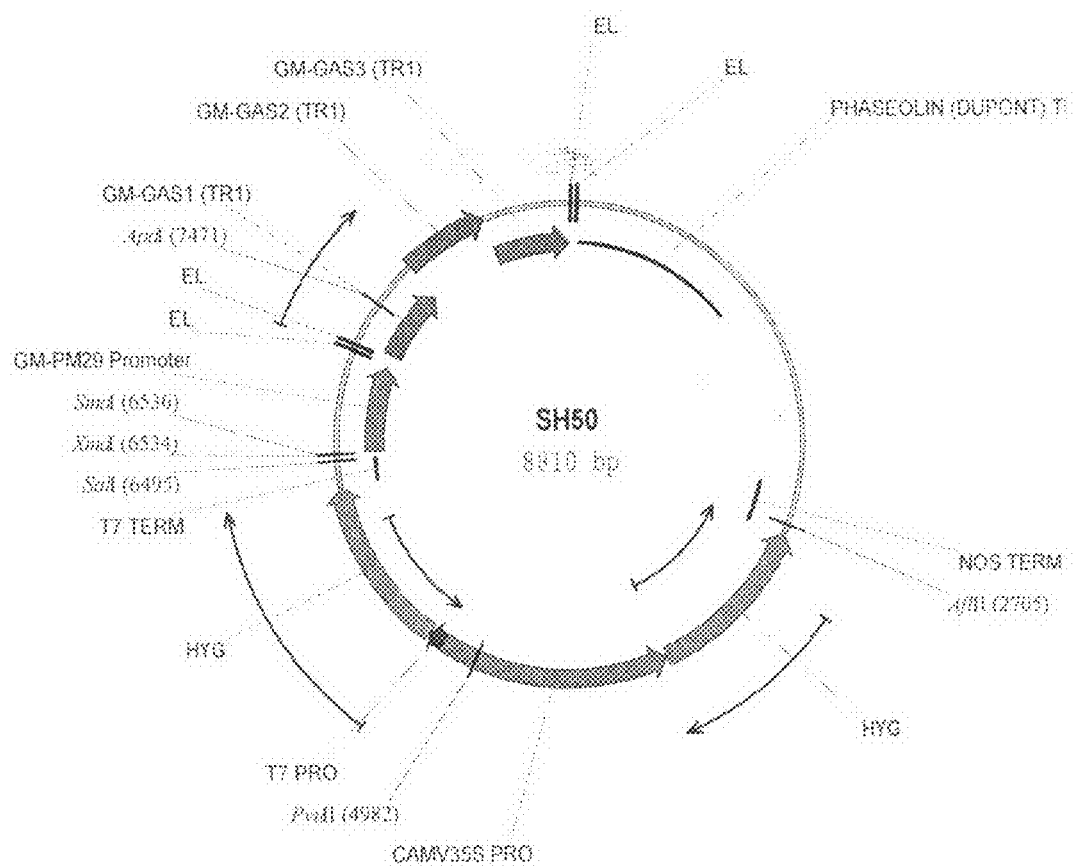

FIG. 9 is a map of plasmid SH50.

Figure 10A:
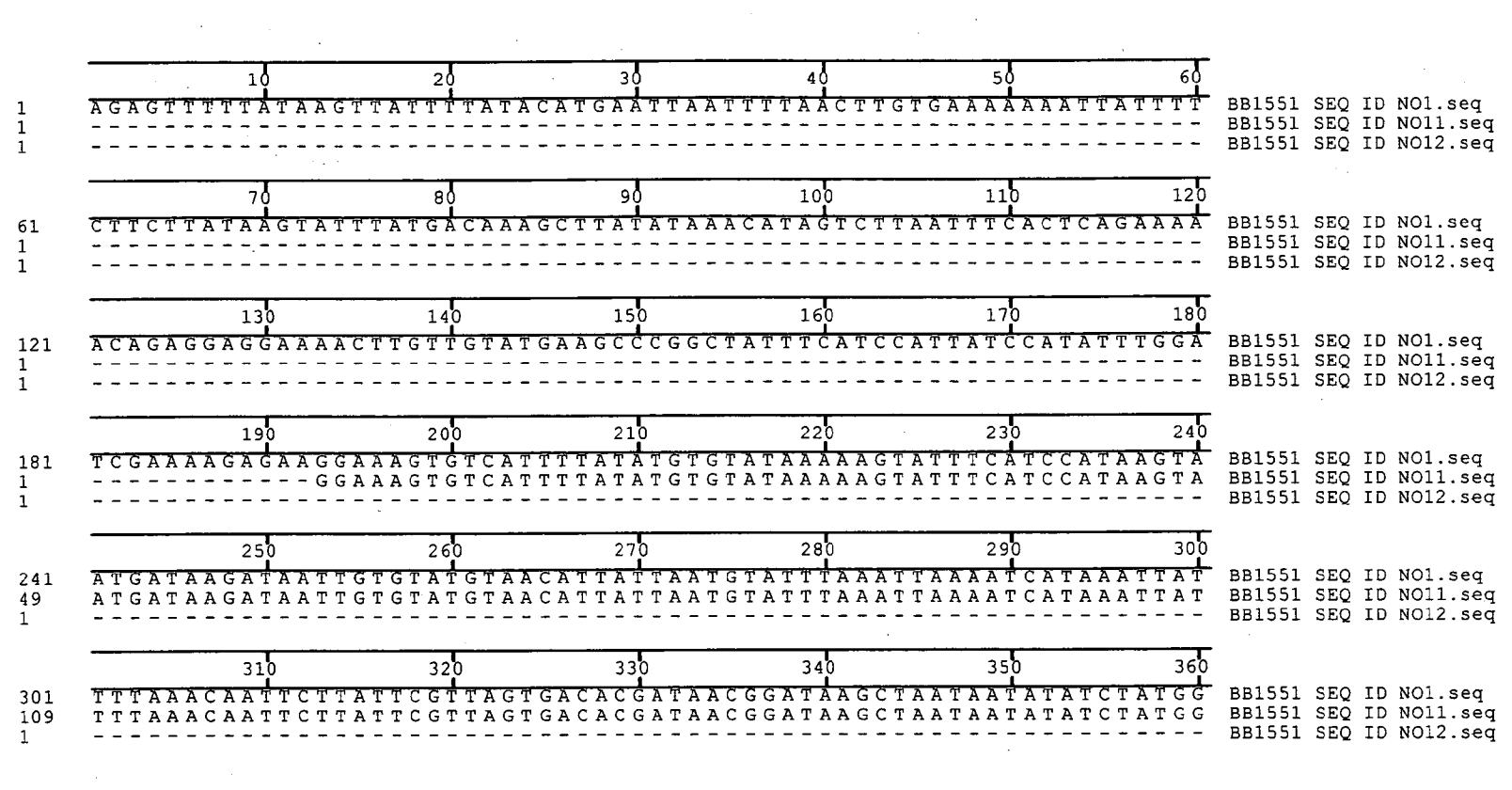
Figure 10B:
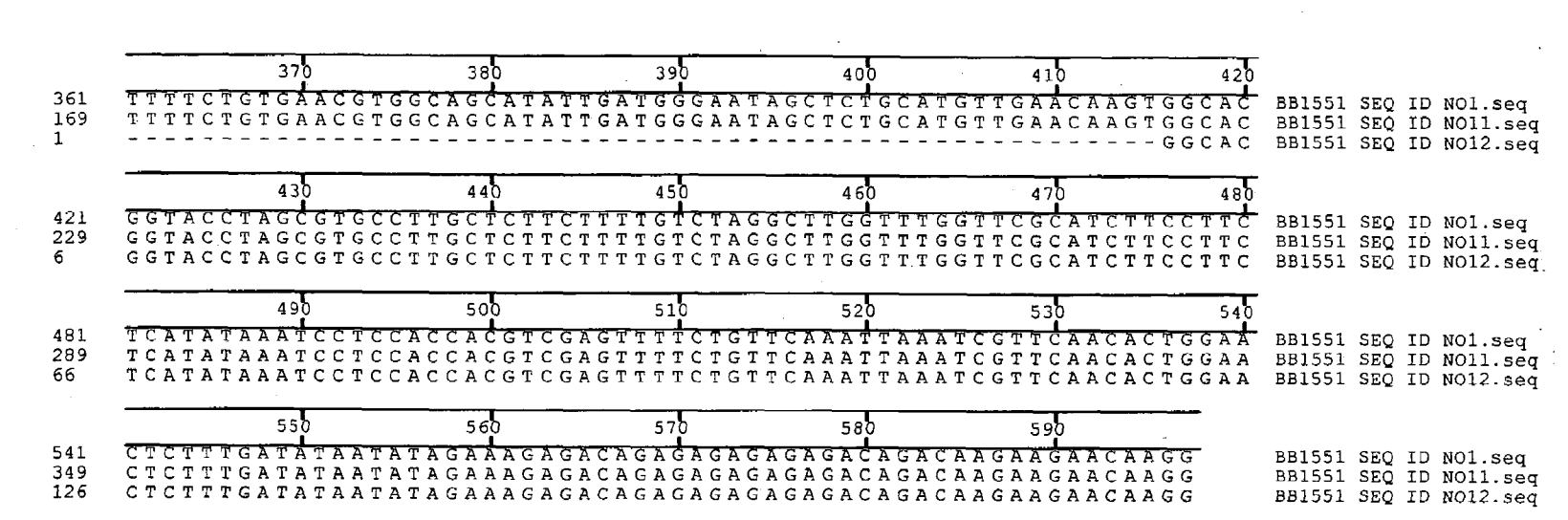

FIGS. 10A and 10B show an alignment of SEQ ID NOs:1, 11 and 12. The ACAC and GTGT elements of SEQ ID NO:15, SEQ ID NO:16, SEQ ID NO:17, SEQ ID NO:18 and SEQ ID NO:19 are marked.

Figure 11:
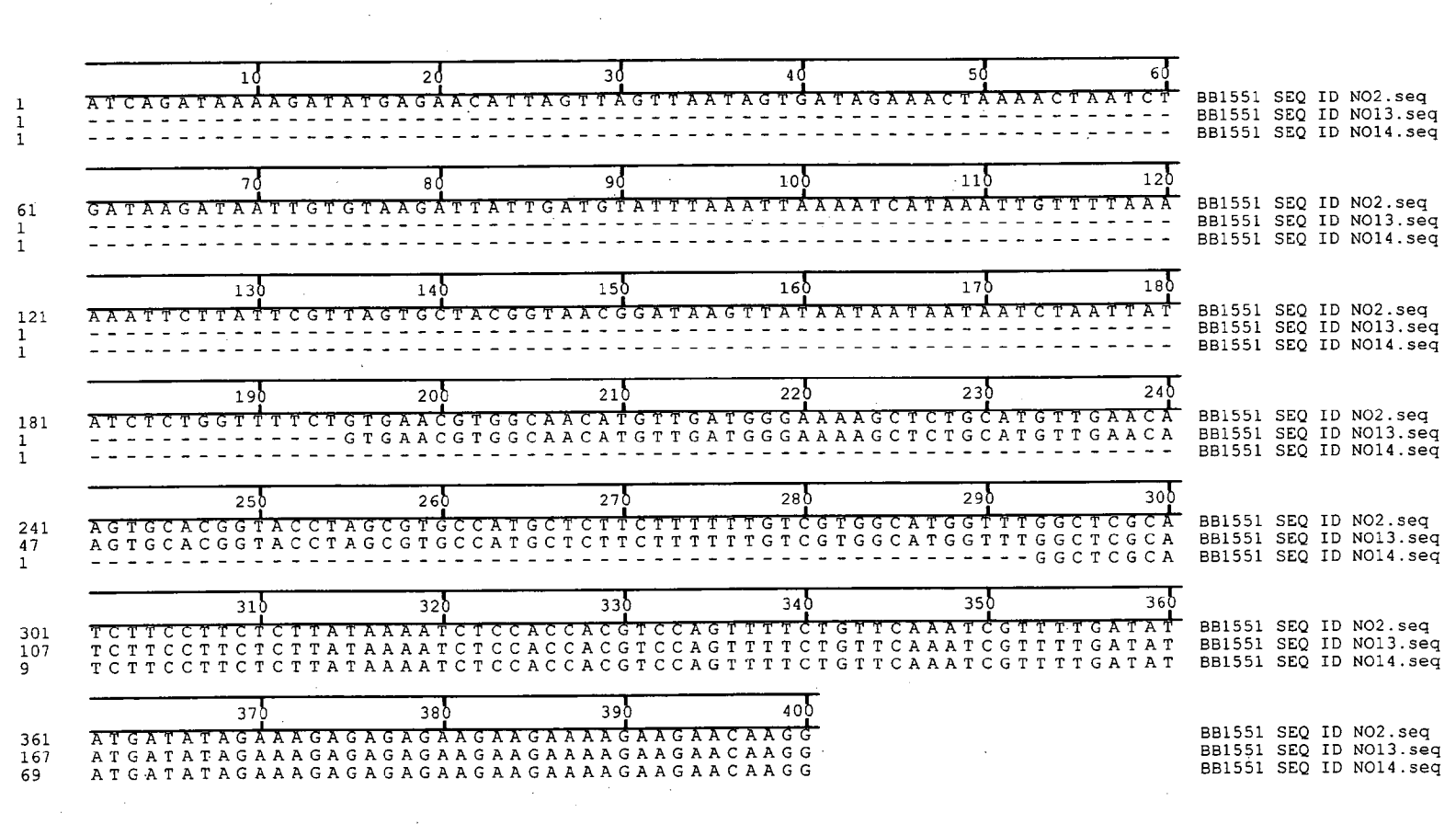

FIG. 11 shows an alignment of SEQ ID NOs:2, 13 and 14. The GTGT element of SEQ ID NO:21 is marked.

DETAILED DESCRIPTION OF THE INVENTION

The disclosure of all patents, patent applications, and publications cited herein are incorporated by reference in their entirety.

In the context of this disclosure, a number of terms shall be utilized.

As used herein, a "PM29 promoter" refers to a promoter of the PM29 polypeptide which is a soybean seed maturation protein (GenBank Accession No. AF117725 for MP29 mRNA).

A "LEA3 promoter" refers to a promoter of the LEA3 polypeptide which is a soybean late-embryogenesis abundant protein (GenBank Accession No. AF004810 for LEA3 mRNA).

The terms "seed-specific promoter" or "seed-preferred promoter", both of which terms may be used interchangeably herein, includes both those promoters active during seed development (such as promoters of seed storage proteins) as well as those promoters active during seed germination.

An "isolated nucleic acid fragment" refers to a polymer of ribonucleotides (RNA) or deoxyribonucleotides (DNA) that is single- or double-stranded, optionally containing synthetic, non-natural or altered nucleotide bases. An isolated nucleic acid fragment in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In *Nucleic Acid Hybridisation*; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 80% to 100%, such as 81%, 82%, 83%, 84%, 85%, 86%, 87%, 88%, 89%, 90%, 91%, 92%, 93%, 94%, 95%, 96%, 98 and 99%.

A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the seed-preferred expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., *Methods Enzymol.* 155:335-350 (1987), and Higuchi, R. In PCR Technology: *Principles and Applications for DNA Amplifications*; Erlich, H. A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp, *CABIOS* 5:151-153 (1989)) with the default parameters (GAP PENALTY=10, GAP LENGTH PENALTY=10). Default parameters for pairwise alignments and calculation of percent identiy of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., *J Mol. Biol.* 215:403-410 (1993)) and Gapped Blast (Altschul, S. F. et al., *Nucleic Acids Res.* 25:3389-3402 (1997)).

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. Functional RNA is including, but not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (*Biochemistry of Plants* 15:1-82 (1989)). It is further recognized that since in most cases the exact boundaries of regulatory sequences have not been completely defined, DNA fragments of some variation may have identical promoter activity. An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

Among the most commonly used promoters are the nopaline synthase (NOS) promoter (Ebert et al., *Proc. Natl. Acad. Sci. U.S.A.* 84:5745-5749 (1987)), the octapine synthase (OCS) promoter, caulimovirus promoters such as the cauliflower mosaic virus (CaMV) 19S promoter (Lawton et al., *Plant Mol. Biol.* 9:315-324 (1987)), the CaMV 35S promoter (Odell et al., *Nature* 313:810-812 (1985)), and the figwort mosaic virus 35S promoter, the light inducible promoter from the small subunit of rubisco, the Adh promoter (Walker et al., *Proc. Natl. Acad. Sci. U.S.A.* 84:6624-66280 (1987), the sucrose synthase promoter (Yang et al., *Proc. Natl. Acad. Sci. U.S.A.* 87:4144-4148 (1990)), the R gene complex promoter (Chandler et al., *Plant Cell* 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., *Cell* 29:1015-1026 (1982)). A plethora of promoters is described in PCT Publication No. WO 00/18963, which published on Apr. 6, 2000, the disclosure of which is hereby incorporated by reference.

Examples of a seed-specific promoter include, but are not limited to, the promoter for β-conglycinin (Chen et al., *Dev. Genet.* 10:112-122 (1989)), the napin promoter, and the phaseolin promoter. Other tissue-specific promoters that may be used to accomplish the invention include, but are not limited to, the chloroplast glutamine synthase (GS2) promoter (Edwards et al., *Proc. Natl. Acad. Sci. U.S.A.* 87:3459-3463 (1990)), the chloroplast fructose-1,6-biophosphatase promoter (Lloyd et al., *Mol. Gen. Genet.* 225:209-2216 (1991)), the nuclear photosynthetic (ST-LS1) promoter (Stockhaus et al., *EMBO J.* 8:2445-2451 (1989)), the serine/threonine kinase (PAL) promoter, the glucoamylase promoter, the promoters for the Cab genes (cab6, cab-1, and cab-1 R, Yamamoto et al., *Plant Cell Physiol.* 35:773-778 (1994); Fejes et al., *Plant Mol. Biol.* 15:921-932 (1990); Lubberstedt et al., *Plant Physiol.* 104:997-1006 (1994); Luan et al., *Plant Cell* 4:971-981 (1992)), the pyruvate orthophosphate dikanase promoter (Matsuoka et al., *Proc. Natl. Acad. Sci. U.S.A.* 90:9586-9590 (1993)), the LhcB promoter (Cerdan et al., *Plant Mol. Biol.* 33:245-255 (1997)), the PsbP promoter (Kretsch et al., *Plant Mol. Biol.* 28:219-229 (1995)), the SUC2 sucrose H+ symporter promoter (Truernit et al., *Planta* 196:564-570 (1995)), and the promoters for the thylakoid membrane genes (psaD, psaF, psaE, PC, FNR, atpC, atpD), etc.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Molecular Biotechnology* 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

"Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065. The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product e.g., a mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

"Antisense inhibition" refers to the production of antisense RNA transcripts capable of suppressing the expression of the target protein.

"Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the over-expressed sequence (see Vaucheret et al., *Plant J.* 16:651-659 (1998); and Gura, *Nature* 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050, which published on Oct. 21, 1999; and PCT Publication No. WO 02/00904, which published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, which published on Aug. 20,1998). Neither of these co-suppressing phenomena have been elucidated mechanistically at the molecular level, although genetic evidence has been obtained that may lead to the identification of potential components (Elmayan et al., *Plant Cell* 10:1747-1757 (1998)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of corn cell transformation is use of particle-accelerated or "gene gun" transformation technology (Klein, T., *Nature* (*London*) 327: 70-73 (1987); U.S. Pat. No. 4,945,050).

"Raffinose saccharides" refer to a group of D-galactose-containing oligosaccharide derivatives of sucrose that are widely distributed in plants. Raffinose saccharides are characterized by the following general formula: [O-β-D-galactopyranosyl-(1→6)$_n$-α-glucopyranosyl-(1→2)-β-D-fructofuranoside where n=0 through n=4 are known respectively as sucrose, raffinose, stachyose, verbascose and ajugose.

Standard recombinant DNA and molecular cloning techniques used herein are well known in the art and are described more fully in Sambrook, J. et al., In *Molecular Cloning: A Laboratory Manual*; 2$^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; *In Current Protocols in Molecular Biology*; John Wiley and Sons: New York, 1990 (hereinafter "Ausubel et al., 1990").

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

A "recombinant expression construct" is a plasmid vector or a fragment thereof comprising the instant soybean seed-specific promoters. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

The PM29 polypeptide is a soybean seed maturation protein (GenBank Accession No. AF117725 for MP29 mRNA) and the LEA3 polypeptide is a soybean late-embryogenesis abundant protein (GenBank Accession No. AF00481 0 for LEA3 mRNA). Although the PM29, or LEA3, polypeptides are known to be present in seeds, the promoters responsible for expression of these polypeptides, and the developmental timing of these promoters, have not been previously described. It was not possible to predict, before the studies reported herein, whether any PM29, or LEA3, gene was controlled by a seed-specific promoter. It is demonstrated herein that seed-specific PM29, or LEA3, promoters do, in fact, exist in plants, and that such promoters can be isolated and used by one skilled in the art.

This invention concerns an isolated nucleic acid fragment comprising a seed-specific plant PM29, or LEA3, promoter. This invention also concerns an isolated nucleic acid fragment comprising a promoter wherein said promoter consists essentially of the nucleotide sequence set forth in SEQ ID NO:1 or SEQ ID NO:2, or said promoter consists essentially of a fragment that is substantially similar and functionally equivalent to the nucleotide sequence set forth in SEQ ID NO:1 or SEQ ID NO:2. A nucleic acid fragment that is functionally equivalent to the instant PM29, or LEA3, promoter is any nucleic acid fragment that is capable of controlling the expression (initiating seed-specific transcription) of a coding sequence or functional RNA in a similar manner to the PM29, or LEA3, promoter. The expression patterns of PM29, or LEA3, promoters are set forth in Examples 1 and 3.

The promoter activity of the soybean genomic DNA fragment upstream of the PM29, or LEA3, protein coding sequence was assessed by linking the fragment to a reporter gene, the *E. coli* β-glucuronidase gene (GUS) (Jefferson, *Plant Mol. Biol. Rep.* 5:387-405 (1987)), transforming the PM29, or LEA3, promoter::GUS expression cassette into *Arabidopsis*, and analyzing GUS expression in various cell types of the transgenic plants (see Example 3). GUS expression was restricted to the seeds although all parts of the transgenic plants were analyzed. These results indicated that the nucleic acid fragment contained seed-specific promoters.

It is clear from the disclosure set forth herein that one of ordinary skill in the art could performing the following procedure:

1) operably linking the nucleic acid fragment containing the PM29, or LEA3, promoter sequence to a suitable reporter gene; there are a variety of reporter genes that are well known to those skilled in the art, including the bacterial GUS gene, the firefly luciferase gene, and the green fluorescent protein gene; any gene for which an easy an reliable assay is available can serve as the reporter gene 2) transforming a chimeric PM29, or LEA3, promoter:: reporter gene expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm.

3) testing for expression of a PM29, or LEA3, promoter in various cell types of transgenic plant tissues, e.g., leaves, roots, flowers, seeds, transformed with the chimeric PM29, or LEA3, promoter::reporter gene expression cassette by assaying for expression of the reporter gene product. A strong seed-specific PM29, or LEA3, promoter will produce high level expression of the reporter in seeds without producing detectable expression in other plant tissues.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention, i.e., any one PM29, or LEA3, promoter or a fragment that is substantially similar and functionally equivalent to any portion of the nucleotide sequence set forth in SEQ ID NOs:1, 2, or 11, to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this invention concerns a recombinant DNA construct comprising at least one galactinol synthase nucleic acid fragment operably linked to any promoter, or combination of promoter elements, of the present invention. Since there are multiple genes encoding galactinol synthases (GAS), it is believed that suppression of more than one gene may be required to detect an effect on raffinose sugar levels. The biosynthesis of raffinose saccharides has been well-characterized (see Dey, P. M. In *Biochemistry of Storage Carbohydrates in Green Plants*; P. M. Dey and R. A. Dixon, Eds.; Academic Press: London, 1985, pp. 53-129). The committed reaction of raffinose saccharide biosynthesis involves the synthesis of galactinol from UDP-galactose and myo-inositol. The enzyme that catalyzes this reaction is galactinol synthase (inositol 1-alpha-galactosyltransferase; EC 2.4.1.123). Synthesis of raffinose and higher homologues in the raffinose saccharide family from sucrose is thought to be catalyzed by distinct galactosyltransferases (for example, raffinose synthase and stachyose synthase). Studies in many species suggest that galactinol synthase is the key enzyme controlling the flux of reduced carbon into the biosynthesis of raffinose saccharides (Handley et al., *J. Amer. Soc. Hort. Sci.* 108:600-605 (1983); Saravitz et al., *Plant Physiol.* 83:185-189 (1987)). Altering the activity of galactinol synthase, either as a result of overexpression or through gene silencing or antisense inhibition, would change the amount of raffinose saccharides produced in a given tissue. The following three genes encoding soybean galactinol synthases have been previously identified: galactinol synthase 1 (U.S. Pat. Nos. 5,773,699 and 5,648,210; Kerr et al, "Nucleotide Sequences of Galactinol Synthase from Zucchini and Soybean"), galactinol synthase 2 (PCT Publication No. WO 2001/077306, which published on Oct. 18, 2001; Allen et al., Plant Raffinose Saccharide Biosynthetic Enzymes) and galactinol synthase 3 (SEQ ID NO:24 of the instant invention).

In another embodiment, this invention concerns host cells comprising either the recombinant DNA constructs of the invention as described herein or isolated polynucleotides of the invention as described herein. Examples of host cells which can be used to practice the invention include, but are not limited to, yeast, bacteria, and plants.

Plasmid vectors comprising the instant recombinant expression constructs can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al., *Plant Cell Rep.* 15:653-657 (1996), McKently et al., *Plant Cell Rep.* 14:699-703 (1995)); papaya (Ling et al., *Bio/technology* 9:752-758 (1991)); and pea (Grant et al., *Plant Cell Rep.* 15:254-258 (1995)). For a review of other commonly used methods of plant transformation see Newell, C.A., *Mol. Biotechnol.* 16:53-65 (2000). One of these methods of transformation uses *Agrobacterium rhizogenes* (Tepfler, M. and Casse-Delbart, F., *Microbiol. Sci.* 4:24-28 (1987)). Transformation of soybeans using direct delivery of DNA has been published using PEG fusion (PCT Publication No. WO 92/17598), electroporation (Chowrira et al., *Mol. Biotechnol.* 3:17-23 (1995); Christou et al., *Proc. Natl. Acad. Sci. U.S.A.* 84:3962-3966 (1987)), microinjection, or particle bombardment (McCabe et al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In *Methods for Plant Molecular Biology*; Academic Press, Inc.: San Diego, CA, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In *Molecular Cloning: A Laboratory Manual;* 2$^{nd}$ ed.; Cold Spring Harbor Laboratory Press: Cold Spring Harbor, N.Y., 1989; Maliga et al., In *Methods in Plant Molecular Biology*; Cold Spring Harbor Press, 1995; Birren et al., In *Genome Analysis: Detecting Genes,* 1; Cold Spring Harbor: N.Y., 1998; Birren et al., In *Genome Analysis: Analyzing DNA*, 2; Cold Spring Harbor: N.Y., 1998; Clark, Ed., In *Plant Molecular Biology: A Laboratory Manual*; Springer: N.Y., 1997).

Figure 1:
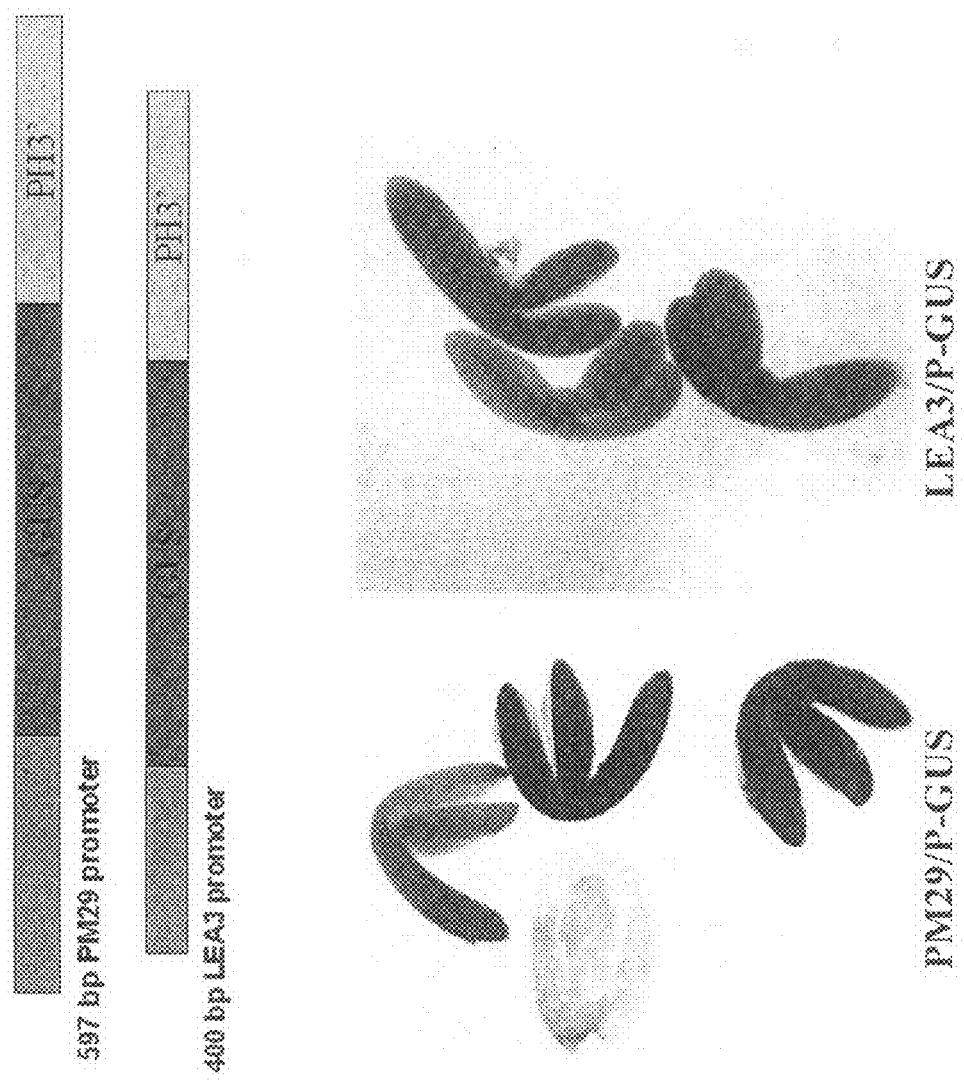

The bacterial GUS gene can be successfully expressed in *Arabidopsis* embryos with both the soybean PM29 and soybean LEA3 promoters (see Example 3 and FIG. 1).

Furthermore, a DNA fragment containing partial sequences of galactinol synthases was also successfully expressed by this promoter in transgenic soybeans. This further validates the application of the PM29, or LEA3, promoter of the invention in plant genetic engineering practice.

The skilled artisan will also recognize that different independent transformation events will result in different levels and patterns of expression of the chimeric genes (Jones et al., *EMBO J.* 4:2411-2418 (1985); De Almeida et al., *Mol. Gen. Genetics* 218:78-86 (1989)). Thus, multiple events must be screened in order to obtain lines displaying the desired expression level and pattern. Such screening may be accomplished by northern analysis of mRNA expression, western analysis of protein expression, or phenotypic analysis. Also of interest are seeds obtained from transformed plants displaying the desired expression profile.

The level of activity of the PM29, or LEA3, promoter is comparable to that of many known strong promoters, such as the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)), the *Arabidopsis* oleosin promoters (Plant et al., *Plant Mol. Biol.* 25:193-205 (1994); Li, Texas A&M University Ph.D. dissertation, pp. 107-128 (1997)), the *Arabidopsis* ubiquitin extension protein promoters (Callis et al., *J. Biol. Chem.* 265(21):12486-12493 (1990)), a tomato ubiquitin gene promoter (Rollfinke et al., *Gene* 211:267-276 (1998)), a soybean heat shock protein promoter, and a maize H3 histone gene promoter (Atanassova et al., *Plant Mol. Biol.* 37:275-285 (1998)).

Expression of chimeric genes in most plant cell makes the PM29, or LEA3, promoter of the instant invention especially useful when seed-specific expression of a target heterologous nucleic acid fragment is required. Another useful feature of the LEA3 promoter is its expression profile in developing seeds. The LEA3 promoter of the invention is most active in developing seeds at late stages (>45 DAF and peaks at seed maturity) and is largely quiescent in early stages (see Table 1). The expression profile of the claimed LEA3 promoter is different from that of a LEA-1 promoter (Lee et al., *Plant Physiol.* 100:2121-2122 (1992)) in that its expression levels remains high at 55 DAF and peaks at maturity whereas LEA-1 expression drops at 55 DAF (Table 1). Furthermore, the LEA3 expression levels are about six to greater than ten fold higher when compared to LEA-1. The PM29 promoter has a more conventional expression profile but remains distinct from other known seed-specific promoters (Table 1). Thus, the PM29, or LEA3, promoter will be a very attractive candidate when gene overexpression, or gene silencing in embryos is desired late in seed development.

Another general application of the PM29, or LEA3, promoter of the invention is to construct chimeric genes that can be used to reduce expression of at least one heterologous nucleic acid fragment in a plant cell. To accomplish this a chimeric gene designed for gene silencing of a heterologous nucleic acid fragment can be constructed by linking the fragment to the PM29, or LEA3, promoter of the present invention. (See U.S. Pat. No. 5,231,020, and PCT Publication No. WO 99/53050, which published on Oct. 21, 1999, PCT Publication No. WO 02/00904, which published on Jan. 3, 2002, and PCT Publication No. WO 98/36083, which published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the PM29, or LEA3, promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:
  (a) transforming a plant cell with the recombinant expression construct described herein;
  (b) growing fertile mature plants from the transformed plant cell of step (a);
  (c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

EXAMPLES

The present invention is further defined in the following Examples, in which parts and percentages are by weight and degrees are Celsius, unless otherwise stated. Techniques in molecular biology were typically performed as described in Ausubel, F. M. et al., In *Current Protocols in Molecular Biology*; John Wiley and Sons: New York, 1990 or Sambrook, J. et al., In *Molecular Cloning: A Laboratory Manual*; $2^{nd}$ ed.; Cold Spring Harbor Laboratory Press: Cold Spring Harbor, N.Y., 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Gene Profiling of Soybean Developing Seeds and Identification of Highly Expressed Genes Late in Seed Development Plant Material:

Developing soybean seeds from cultivar 'Jack' were harvested at 15, 20, 30, 40, 45, 50, 55 days after flowering (DAF) and at maturation. Seeds were harvested, immediately flash frozen in liquid nitrogen and stored at minus 80° C. until used. Total RNA was extracted followed by isolation of poly A+ RNA using standard molecular biology techniques (Sambrook et al., 1989).

Gene Profiling using Lynx MPSS:

The goal was to identify genes that are highly expressed very late in seed development (50 DAF and later) and to isolate the promoters driving these genes. The Lynx MPSS transcript profiling technique was used (Brenner et al., *Proc Natl Acad Sci USA* 97:1665-70 (2000)) to determine gene expression at each developmental stage. A soybean (*Glycine max*) seed maturation protein (PM29) and a soybean (*Glycine max*) late embryogenesis abundant protein (LEA3) were identified that showed peak expression after 50 DAF (see Table 1). Table 1 shows the gene expression profile of *Glycine max* PM29 and *Glycine max* LEA3 as well as the profiles of highly expressed genes of which the promoters are used in a wide range of applications. Promoter isolation of these genes have been described for Kti (Jofuku et al., *Plant Cell* 1:1079-1093 (1989)), β-conglycinin (Chen et al., *Dev. Genet.* 10:112-122 (1989)), 2S albumin (U.S. Pat. No. 6,177,613 B1), P34 (US Application No. 2004/0158052 A1; PCT Publication No. WO 2004/071178, which published on Aug. 26, 2004), Annexin (US Application No. 2004/0158052 A1; PCT Publication No. WO 2004/071178, which published on Aug. 26, 2004), Glycinin (*Plant Cell* 1:313-328 (1989)), and LEA-1 (Lee et al., *Plant Physiol.* 100: 2121-2122 (1992); GenBank Accession No. M97285)

TABLE 1

Lynx MPSS Profiles*

| Name | 15 DAF | 20 DAF | 30 DAF | 40 DAF | 45 DAF | 50 DAF | 55 DAF | Mature |
|---|---|---|---|---|---|---|---|---|
| LEA3 | 0 | 124 | 132 | 563 | 1581 | 6276 | 8326 | 33562 |
| PM29 | 109 | 0 | 0 | 6 | 28 | 138 | 4282 | 559 |
| Kti3 | 23058 | 86345 | 148901 | 64330 | 66178 | 13999 | 611 | 458 |
| 2S albumin | 12 | 4425 | 7641 | 8366 | 4907 | 1547 | 21 | 39 |
| P34 | 4743 | 75046 | 74118 | 66468 | 48441 | 10169 | 3345 | 2572 |
| Annexin | 2099 | 864 | 590 | 310 | 329 | 5 | 8 | — |
| Glycinin G1 | 2789 | 68927 | 68782 | 71171 | 68995 | 43454 | 1317 | 997 |
| Glycinin Gy4 | 144 | 18595 | 24049 | 35909 | 20137 | 7327 | 91 | 318 |
| β-conglycinin alpha'- unit | 6005 | 44197 | 32918 | 25879 | 19274 | 7942 | 650 | 874 |
| β-conglycinin beta unit | — | — | 375 | 11854 | 5978 | 495 | — | 235 |
| LEA-1 | — | — | 8 | 177 | 471 | 1264 | 57 | 3254 |

*Lynx MPSS profiles (expressed as adjusted PPM) of a soybean (Glycine max) seed maturation protein (PM29) and a soybean (Glycine max) late embryogenesis abundant protein (LEA3) during soybean seed development (DAF = days after flowering; mature = mature seed). Lynx MPSS profiles of seed storage proteins are included for comparison.

The results shown in Table 1 demonstrate that LEA3 expression increases during late development and peaks at maturity whereas PM29 increases during late development and peaks at 55 DAF. Transcript levels of LEA3 are about six to greater than ten fold higher when compared to LEA-1.

Example 2

Isolation of Soybean PM29 and LEA3 Promoters

The promoters of a soybean seed maturation protein PM29 and a soybean late-embryogenesis abundant protein LEA3 were isolated using a polymerase chain reaction (PCR) based approach. Soybean genomic DNA was digested to completion with a DNA restriction enzyme that generates blunt ends (DraI, EcoRV, PvuII or StuI, for example) according to standard protocols. The Universal GenomeWalker™ kit from Clonetech™ (Product User Manual No. PT3042-1) was used to ligate adaptors to the ends of the genomic DNA fragments. Nested primers are also supplied in the Universal GenomeWalker™ kit that are specific for the adaptor sequence (AP1 and AP2, for the first and second adaptor primer, respectively). Two gene specific primers (GSP1 and GSP2) were designed for the soybean PM29 gene based on the 5' coding sequences in PM29 cDNA in DuPont EST database. The oligonucleotide sequences of the GSP1 and GSP2 primers (SEQ ID NO:3 and SEQ ID NO:4, respectively) have the sequences shown as follows:

```
SEQ.ID NO:3
5'-TCTTCTGTTCTTGCCGTTGCTTTCTC-3'

SEQ ID NO:4
5'-CGCGGATCCGACTTGCTCCTTGGCAGCACTGGT-3'
```

The underlined bases are the recognition site for the restriction enzyme BamH I. The AP2 primer from the Universal GenomeWalker™ kit contains a Sal I restriction site.

The AP1 and the GSP1 primers were used in the first round PCR using each of the adaptor ligated genomic DNA populations (DraI, EcoRV, PvuII or StuI) under conditions defined in the GenomeWalker™ protocol. Cycle conditions were 94° C. for 4 minutes; 94° C. for 2 seconds and 72° C. for 3 minutes, 7 cycles; 94° C. for 2 seconds and 67° C. for 3 minutes, 32 cycles; 67° C. for 4 minutes. The products from each of the first run PCRs were diluted 50-fold. One microliter from each of the diluted products was used as templates for the second PCR with the AP2 and GSP2 as primers. Cycle conditions were 94° C. for 4 minutes; 94° C. for 2 seconds and 72° C. for 3 minutes, 5 cycles; 94° C. for 2 seconds and 67° C. for 3 minutes, 20 cycles; 67° C. for 3 minutes. Agarose gels were run to determine which PCR gave an optimal fragment length. A 679 bp genomic fragment was detected and isolated from the EcoRV-digested genomic DNA reaction. The genomic fragment was digested with BamH I and Sal I and cloned into Bluescript KS+ vector for sequencing. Finally, sequencing data indicated that this genomic fragment contained a 597 bp soybean PM29 promoter sequence as shown in SEQ ID NO:1.

Two gene specific primers (GSP3 and GSP4) were designed for the soybean LEA3 gene based on the 5' coding sequences in LEA3 cDNA in DuPont EST database. The oligonucleotide sequences of the GSP3 and GSP4 primers (SEQ ID NO:5 and SEQ ID NO:6, rspectively) have the sequences shown as follows:

```
SEQ ID NO:5
5'-TCTTCTGTTCTTGCCGTTGCTTTCTC-3'

SEQ ID NO:6
5'-CGCGGATCCCGACTTGTTCCTTGGCAGCACTTGC-3'
```

The AP1 and the GSP3 primers were used in the first round PCR using the same conditions defined in the Universal GenomeWalker™ kit protocol with the same cycle conditions used for soybean PM29 promoter described above. A 483 bp genomic fragment was amplified and isolated from the EcoRV-digested GenomeWalker library. The genomic fragment was digested with BamH I and Sal I and cloned into Bluescript KS+ vector for sequencing. Sequencing data indicated that this genomic fragment contained a 400 bp soybean LEA3 promoter sequence as shown in SEQ ID NO:2.

Example 3

Construction of GUS Reporter Constructs Linked to Soybean PM29 Promoter or Soybean LEA3 Promoter and Expression in *Arabidopsis* Seeds Two oligonucleotides were designed to re-amplify the PM29 promoter with either BamH I or Nco I sites (underlined below in SEQ ID NO:7 and SEQ ID NO:8, respectively). The oligonucleotide sequences of these two oligonucleotides are shown as follows:

```
SEQ ID NO:7
5'-CGCGGATCCAGAGTTTTTATAAGTTATTTTATACATGAATTA-3'

SEQ ID NO:8
5'-CCTTGACCATGGTTGTTCTTCTTGTCTGTCTCTCTCTCT-3'
```

The re-amplified PM29 promoter fragment was digested with BamH I and Nco I, purified and cloned into the BamH I and Nco I sites of plasmid pG4G (FIG. 8) to make the fusion between the soybean PM29 promoter-GUS fusion (pSH43). The plasmid pG4G has been described in U.S. No. 5,968,793, the contents of which are hereby incorporated by reference.

Two oligonucleotides with either BamH I or Nco I sites at the 5' ends were designed to re-amplify the LEA3 promoter (underlined below in SEQ ID NO:9 and SEQ ID NO:10, respectively). The oligonucleotide sequences of these two PCR primers are shown as follows:

```
SEQ ID NO:9
5'-CGCGGATCCATCAGATAAAAGATATGAGAACATTAGTTAG-3'

SEQ ID NO:10
5'-CCTTGACCATGGTTGTTCTTCTTTTCTTCTTCTCTCTCTTT-3'.
```

The re-amplified LEA3 promoter fragment was digested with BamH I and Nco I, purified and cloned into the BamH I and Nco I sites of plasmid pG4G to make the fusion between the soybean LEA3 promoter-GUS fusion (pSH42).

The chimeric promoter-GUS recombinant constructs were cloned as a BamH I-Sal I fragment into the *Agrobacterium tumefaciens* binary vector pZBL120 to create pZBL202 and pSH41, respectfully. The binary vector pZBL120 is the same as the pZBL1 binary vector as described in U.S. Pat. No. 5,968,793 (American Type Culture Collection Accession No. 209128), except the NOS promoter was replaced with a 963 bp 35S promoter (NCBI Accession No. V00141 (also known as NCBI General Indentifier No. 58821) from nucleotide 6494 to 7456) in the Nos/P-nptll-OCS 3' gene. The new 35S promoter-nptll-OCS 3' gene serves as a kanamycin (Kan) resistance plant selection marker in pZBL120. The pZBL202 and pSH41 binary vector constructions were transformed into *Agrobacterium tumefaciens* LBA4404, which was then used to inoculate *Arabidopsis* plants by vacuum infiltration (Ye, Guang-Ning et al., *Plant Journal* 19:249-257 (1999)). The *Arabidopsis* seeds of primary transformants were selected by 100 mg/L Kan on MS culture plates. The Kan resistant seedlings were transferred into soil and analyzed for GUS activity in seeds, leaves, stems, flowers and silique coats. The GUS activity was analyzed by histochemical staining by X-Gluc and quantitative fluorometric MUG GUS assay as described by Jefferson (*Plant Mol. Biol. Rep.* 5:387-405 (1987)).

As shown in FIG. 1, both soybean PM29 promoter and soybean LEA3 promoter provide very specific GUS expression in seeds (dark seeds are stained blue in the FIG. 1). Other parts of transformed plants, such as leaves, stems, flowers and silique coats, did not exhibit GUS staining (data not shown). Analysis of the relative promoter strengths in seeds is performed by quantitative fluorometric MUG GUS assay (see Table 2). The PM29 promoter is stronger than the LEA3 promoter is for seed-specific expression. Although the PM29 and the LEA3 promoters are not as strong as the seed storage protein Glycinin 1 promoter, their temporal expression patterns are more towards late seed development stage and maturity as compared to the mid- to late-development stage by Glycinin 1 promoter (see Table 1).

TABLE 2

Relative Promoter Strengths

| Promoter | GUS (pmol MU/µg protein · hour) | Standard Deviation |
|---|---|---|
| PM29 | 2022.4 | 1495.8 |
| LEA3 | 1168.9 | 674.1 |
| Annexin | 770.1 | 445.6 |
| P34 | 75.2 | 81.4 |
| BC-beta | 12.4 | 5.6 |
| Glycinin1 | 8961.9 | 4504.4 |

Example 4

Identification of Seed-Specific Consensus Elements in PM29 and LEA3 Promoters

The soybean PM29 promoter contains the consensus core promoter sequences known as TATA box and transcription start site. The PM29 promoter also contains several seed-specific/ABA responsive elements, such as the RY-G-box seed-specific coupling elements (CATGMT, CATGTTG, GAACGTGGC), ACAC elements (GTGACACGAT (SEQ ID NO:15), TCAACACTGG (SEQ ID NO:16)), GTGT elements (AAAGTGTCAT (SEQ ID NO:17), TATGTGTATA (SEQ ID NO:18), ATTGTGTATG (SEQ ID NO:19)) and AT-rich sequences. All these conserved elements, individually or in combination, can be important for the temporal and tissue-specific gene expression of the soybean PM29 promoter.

The soybean LEA3 promoter contains the consensus core promoter sequences known as TATA box and transcription start site. The LEA3 promoter also contains several seed-specific/ABA responsive elements, such as the RY-G-box seed-specific coupling elements (AACATGTTG, TGCATGTTG, GCCATGCTC, GGCATGGTT, TGAACGTGGC (SEQ ID NO:20)), and a GTGT element (ATTGTGTAAG (SEQ ID NO:21)). All these conserved elements, individually or in combination, can be important for the temporal and tissue-specific gene expression of the soybean LEA3 promoter.

Example 5

Deletion and Site-directed Mutagenesis of PM29 and LEA3 Promoters

To further define the transcriptional elements controlling temporal and tissue-specific gene expression of these new soybean seed-specific promoters, two 5' unidirectional deletion fragments of the soybean PM29 promoter were made using PCR with the promoter fragment length 405 bp and 182 bp (SEQ ID NO:11 and SEQ ID NO:12, respectively). For the LEA3 promoter, another two deletion fragments were made with the fragment length 206 bp and 108 bp (SEQ ID NO:13 and SEQ ID NO:14, respectively). All these deletion promoter-GUS constructs were transferred into binary vectors and were transformed into transgenic Arabidopsis (as described in Example 3). Analysis of the relative promoter strengths and their tissue-specificity of expression are performed by histochemical GUS staining with X- Gluc (as described in Example 3).

Applicants results indicated that the 405 bp truncated PM29 promoter (SEQ ID NO:11) can still provide a very strong seed specific expression at a strength comparable to the 597 bp PM29 promoter (SEQ ID NO:1) and the 182 bp truncated PM29 promoter (SEQ ID NO:12) lost its promoter activity (see FIGS. 10A and 10B). These results suggested the ACAC, GTGT and RY-G-box-seed-specific coupling elements described in Example 4 (see SEQ ID NO:15, SEQ ID NO:17, SEQ ID NO:18, SEQ ID NO:19 and SEQ ID NO:20) are important in the PM29 promoter function. However, our data also indicated that one ACAC element (SEQ ID NO:16) by itself is not sufficient for the promoter activity. Synergistic interactions between these elements are important for the PM29 promoter function.

For the LEA3 promoter, both the 206 bp (SEQ ID NO:13) and the 108 bp (SEQ ID NO:14) truncated promoters lost their promoter activities, which suggested again that the GTGT element described in Example 4 (see SEQ ID NO:21) is important in the LEA3 promoter activity (see FIG. 11). However, our data also indicated that one RY-G-box-seed-specific coupling element (SEQ ID NO:20) by itself is not sufficient for the promoter activity. Synergistic interactions between the GTGT and the RY-G-box-seed-specific coupling elements are important for the LEA3 promoter function.

Table 3 shows the nucleotide locations on PM29 (SEQ ID NO:1) and LEA3 (SEQ ID NO:2) of the ACAC and GTGT elements and part of the RY-G-box-seed-specific coupling element (SEQ ID NOs:15-21).

TABLE 3

Element Locations on PM29 and LEA3

| SEQ ID NO: | Nucleotide location | PM29 or LEA3 |
|---|---|---|
| SEQ ID NO: 15 | 323-332 | PM29 |
| SEQ ID NO: 16 | 529-538 | PM29 |
| SEQ ID NO: 17 | 195-204 | PM29 |

TABLE 3-continued

Element Locations on PM29 and LEA3

| SEQ ID NO: | Nucleotide location | PM29 or LEA3 |
|---|---|---|
| SEQ ID NO: 18 | 209-218 | PM29 |
| SEQ ID NO: 19 | 252-261 | PM29 |
| SEQ ID NO: 20 | 368-377 | PM29 |
| SEQ ID NO: 20 | 196-205 | LEA3 |
| SEQ ID NO: 21 | 70-79 | LEA3 |

Example 6

Construction of Galactinol Synthase Silencing Plasmids Driven by LEA3 and PM29

Raffinose saccharides are a group of D-galactose-containing oligosaccharide derivatives of sucrose that are widely distributed in plants. Raffinose saccharides are characterized by the following general formula: [O-β-D-galactopyranosyl -(1→6)$_n$-α-glucopyranosyl-(1→2)-β-D-fructofuranoside where n=0 through n=4 are known respectively as sucrose, raffinose, stachyose, verbascose and ajugose.

Although abundant in many species, raffinose saccharides are an obstacle to the efficient utilization of some economically important crop species. Raffinose saccharides are not digested directly by animals, primarily because alpha-galactosidase is not present in the intestinal mucosa (Gitzelmann et al., *Pediatrics* 36:231-236 (1965); Rutloff et al., *Nahrung* 11:39-46 (1967)). However, microflora in the lower gut are readily able to ferment the raffinose saccharides resulting in an acidification of the gut and production of carbon dioxide, methane and hydrogen gases (Murphy et al., *J. Agr. Food. Chem.* 20:813-817 (1972); Cristofaro et al., In *Sugars in Nutrition*; H. L. Sipple and K. W. McNutt, Eds. Academic Press: New York, Chap. 20, 1974; pp. 313-335; Reddy et al., *J. Food Science* 45:1161-1164 (1980)). The resulting flatulence can severely limit the use of leguminous plants in animal, particularly human, diets. It is unfortunate that the presence of raffinose saccharides restricts the use of legumes in human diets because many of these species are otherwise excellent sources of protein and soluble fiber. Varieties of edible beans free of raffinose saccharides would be more valuable for human and animal diets and would facilitate broader access to the desirable nutritional qualities of edible leguminous plants.

The biosynthesis of raffinose saccharides has been well-characterized (see Dey, P. M. In *Biochemistry of Storage Carbohydrates in Green Plants*; P. M. Dey and R. A. Dixon, Eds.; Academic Press: London, 1985, pp. 53-129). The committed reaction of raffinose saccharide biosynthesis involves the synthesis of galactinol from UDP-galactose and myo-inositol. The enzyme that catalyzes this reaction is galactinol synthase (inositol 1-alpha-galactosyltransferase; EC 2.4.1.123). Synthesis of raffinose and higher homologues in the raffinose saccharide family from sucrose is thought to be catalyzed by distinct galactosyltransferases (for example, raffinose synthase and stachyose synthase). Studies in many species suggest that galactinol synthase is the key enzyme controlling the flux of reduced carbon into the biosynthesis of raffinose saccharides (Handley et al., *J. Amer. Soc. Hort. Sci.* 108:600-605 (1983); Saravitz et al., *Plant Physiol.* 83:185-189 (1987)). Altering the activity of galactinol synthase, either as a result of overexpression or through gene silencing or antisense inhibition, would change the amount of raffinose saccharides produced in a given tissue.

Three genes encoding soybean galactinol synthases have been previously identified: galactinol synthase 1 (U.S. Pat. Nos. 5,773,699 and 5,648,210; Kerr et al, "Nucleotide Sequences of Galactinol Synthase from Zucchini and Soybean" ), galactinol synthase 2 (PCT Publication No. WO 2001/077306, which published on Oct. 18, 2001; Allen et al., Plant Raffinose Saccharide Biosynthetic Enzymes) and galactinol synthase 3 (SEQ ID NO:24 of the instant invention). Since there are multiple genes encoding galactinol synthases (GAS), it is believed that suppression of more than one gene may be required to detect an effect on raffinose sugar levels.

Preparation of pJMS10:

Polynucleotide fragments encoding parts of the soybean galactinol synthase 1 (GAS1) (SEQ ID NO:22 which is identical to SEQ ID NO:6 of U.S. Patent Nos. 5,773,699 and 5,648,210), galactinol synthase 2 (GAS2) in clone ses4d.pk0017.b8 (SEQ ID NO:23 which is identical to SEQ ID NO:3 of PCT Publication No. WO 2001/077306, which published on Oct. 18, 2001) and galactinol synthase 3 (GAS3) (SEQ ID NO:24) were amplified by standard PCR methods using Pfu Turbo DNA polymerase (Stratagene, La Jolla, Calif.) and the following primer sets. The GAS1 oligonucleotide primers were designed to add a Not1 restriction endonuclease site at the 5' end and a stopcodon (TGA) and an Xho1 site to the 3' end (SEQ ID NO:25 and SEQ ID NO:26, respectively). The DNA sequence comprising the 518 bp polynucleotide from soybean GAS1 is shown in SEQ ID NO:27. The GAS2 oligonucleotide primers were designed to add an Xho1 restriction endonuclease site at the 5' end and a stopcodon (TAA) and a Pst1 site to the 3' end (SEQ ID NO:28 and SEQ ID NO:29, respectively). The DNA sequence comprising the 519 bp polynucleotide from soybean GAS2 is shown in SEQ ID NO:30. The GAS3 oligonucleotide primers were designed to add a Pst1 restriction endonuclease site at the 5' end and a stopcodon (TAG) and a Not1 site to the 3' end (SEQ ID NO:31 and SEQ ID NO:32, respectively). The DNA sequence comprising the 519 bp polynucleotide from soybean GAS3 is shown in SEQ ID NO:33.

Figure 2:
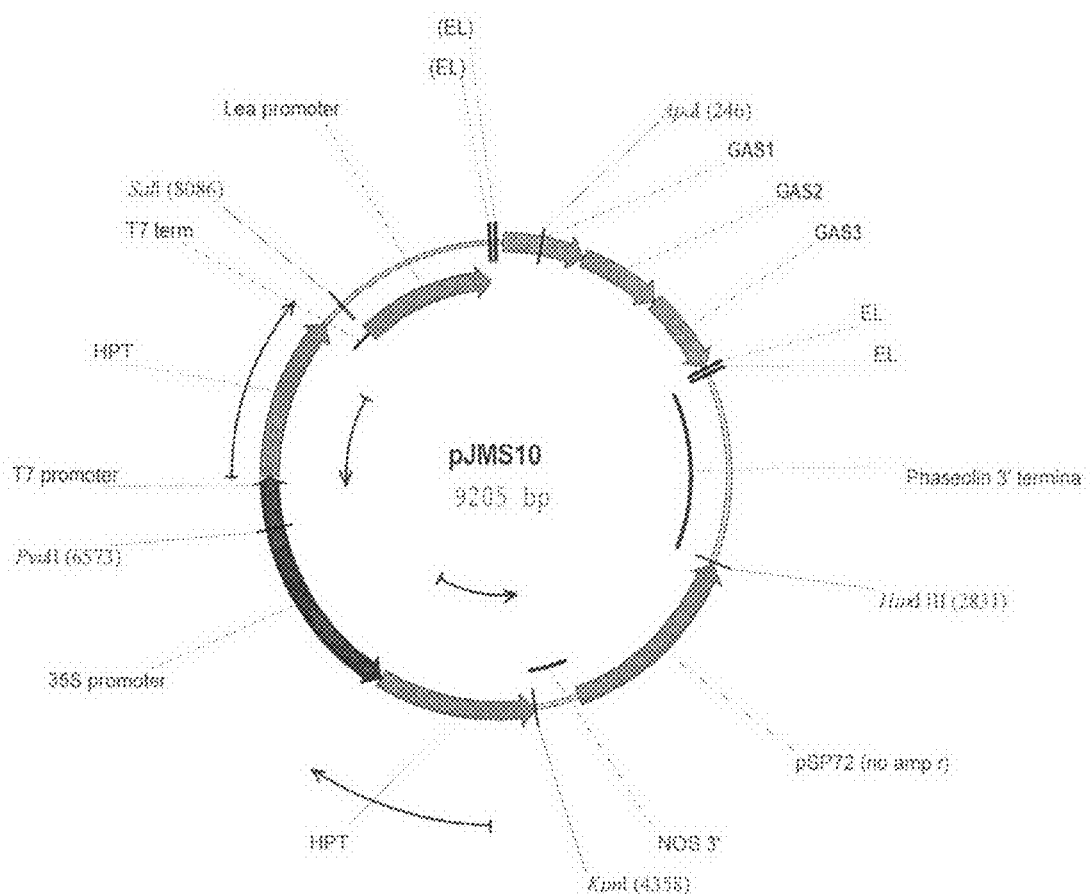
FIG. 2 is a map of plasmid pJMS10.

The polynucleotide products for GAS1 (SEQ ID NO:27), GAS2 (SEQ ID NO:30) and GAS3 (SEQ ID NO:33) obtained from the amplifications described above were digested with Not1, Xho1 and Pst1 and assembled into vector pJMS10 (FIG. 2) by the following steps. From plasmid KS123 (prepared according to US Application No. 2004/0073975 A1, which published on Apr. 15, 2004) the HindIII cassette containing the beta-conglycinin promoter-phaseolin terminator was removed creating the plasmid KS120. To the unique BamHI site of plasmid KS120 a LEA promoter-phaseolin terminator was inserted as a BamHI fragment creating plasmid KS127. The LEA promoter (Lee et al., *Plant Physiol.* 100:2121-2122 (1992); GenBank Accession No. M97285) was amplified from genomic A2872 soybean DNA and a phaseolin 3' end was added as described in U.S. Patent Publication No. 2003/0036197 A1. To KS127 an EL linker was added to a unique Not1 site as described in U.S. Patent Publication No. 2003/0036197 A1, creating plasmid KS139. To KS139 an EL linker was added to a unique Not1 site as described in U.S. Patent Publication No. 2003/0036197 A1, creating plasmid KS147. Plasmid KS147 also comprises nucleotides encoding hygromycin phosphotransferase (HPT) under the control of the T7 promoter and termination signals and the 35S promoter and Nos 3'. Next the isolated DNA fragments containing partial sequences of GAS1 (SEQ ID NO:27), GAS2 (SEQ ID NO:30) and GAS3 (SEQ ID NO:33) were inserted into the Not1-digested plasmid KS147 to obtain plasmid pJMS10 (FIG. 2).

Preparation of SH56, SH55 and SH49:

Plasmids pSH42 and pSH43 (described in Example 3) were digested with NcoI (located at the 3' end of the promoter), filled in with vent polymerase (obtained from New England Biolabs Inc.) and subsequently digested with BamHI (5' end of the promoter). The resulting promoter fragments were isolated and cloned into pBluescript 11 SK (+) (Stratagene, Inc.) previously cut with XbaI (and filled in by vent polymerase) and BamHI creating the plasmids pBluescriptLEA3 and pBluescriptPM29, respectively. These constructs contain a unique Not1 site at the 3' end of the promoter. Two copies of the Eag1-ELVISLIVES sequence (SEQ ID NO:34) was added on the 5' site of the Not1 site as described in EP1297163 A2 (PCT Publication No. WO 2002/000904, which published Jan. 3, 2002). The nucleotide sequence of SEQ ID NO:34 is shown as follows (restriction sites listed above sequence):

```
   Eag1                                          Eag1
cggccg gagctggtcatctcgctcatcgtcgagtcg gcggccg Not1
gagctggtcatctcg ctcatcgtcgagtcg gcggccgc
```

Figure 3:
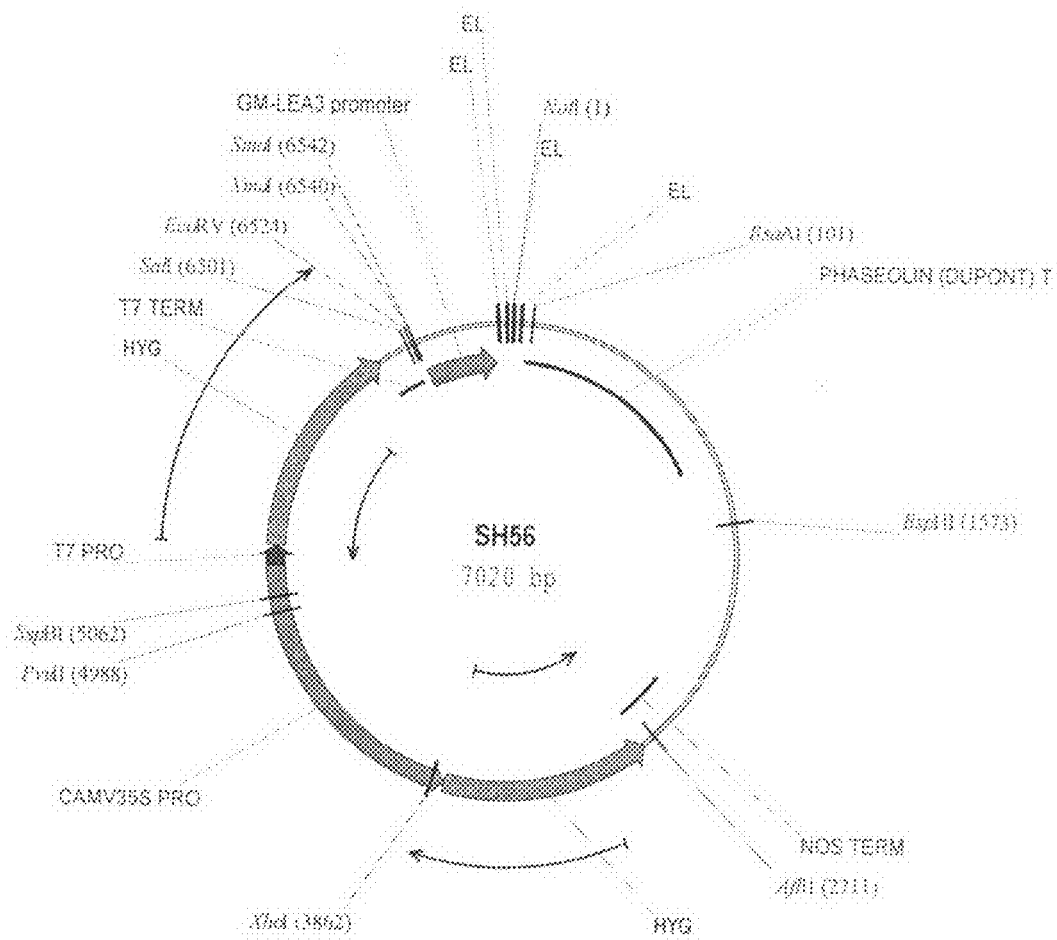
FIG. 3 is a map of plasmid SH56 (LEA3 promoter-ELEL-Not1-ELEL-phaseolin terminator).
Figure 4:
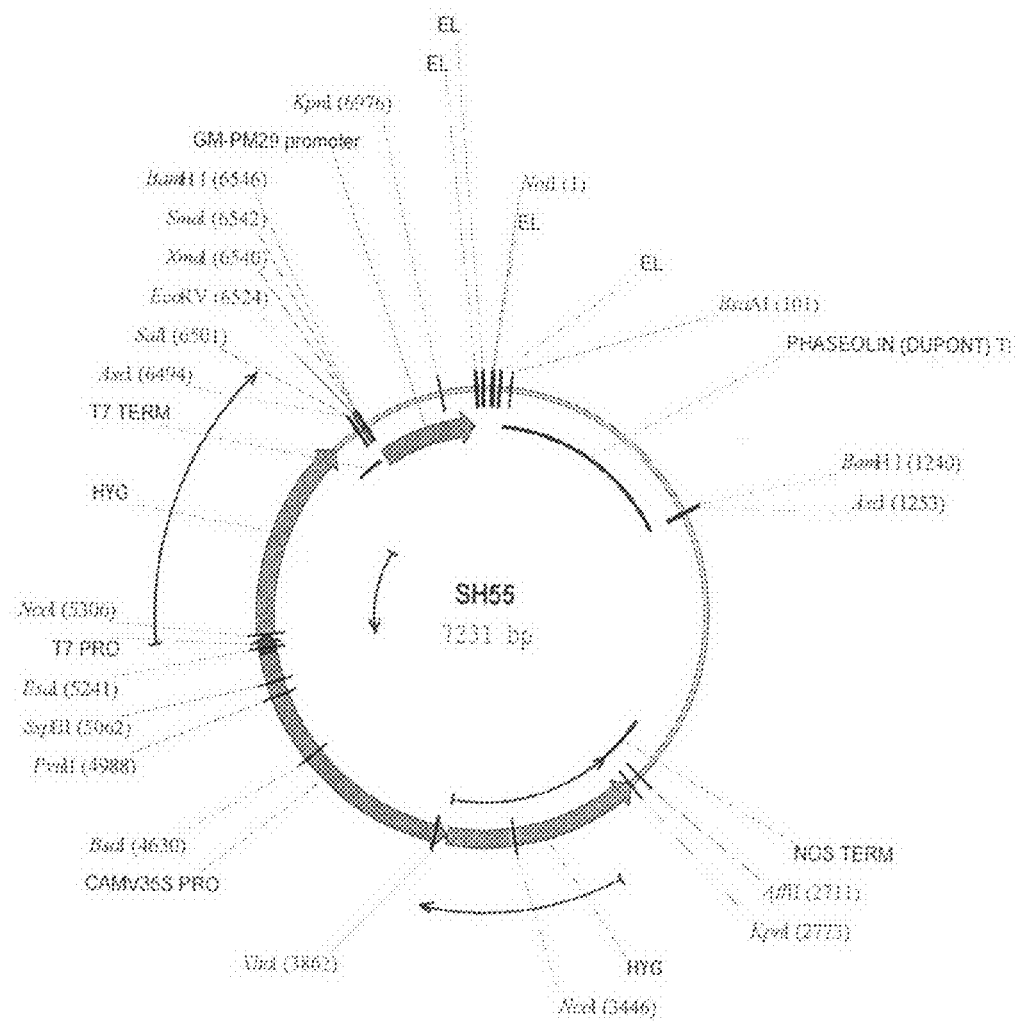
FIG. 4 is a map of plasmid SH55 (PM29 promoter-ELEL-Not1-ELEL-Phaseolin terminator).

The promoter fragments were isolated using a BamHI/Not1 digestion and ligated into pJMS10 plasmid previously cut with BamH1 (partial) and Not1. The pJMS10 plasmid also contains the complementary strand of SEQ ID NO:34 (SEQ ID NO:39) 3' of the Not1 site. This ligation resulted in the following plasmids: SH56 (LEA3 promoter-ELEL-Not1-ELEL-phaseolin terminator, see FIG. 3), SH55 (PM29 promoter-ELEL-Not1-ELEL-Phaseolin terminator, see FIG. 4) and SH49. SH49 is identical to SH55 with the exception of a truncated ELEL sequence (SEQ ID NO:35) at the 3' border of the Not1. The truncated sequence is missing the "tgacca" of the ELEL sequence at the 3' border of the Not1 and was identified after sequence verification of the plasmid and probably originated during the PCR amplification of the ELEL linker. This truncation has no effect on the ability of silencing the GAS genes as is evident from Example 7. The nucleotide sequence of SEQ ID NO:35 is shown as follows (restriction sites listed above sequence):

```
 Not1                                            Eag1
gcggccgc cgactcgacgatgagcgagatgaccagctc cggccg missing "tgacca" ⇓
ccgactcgacgatgagcgaga gctc
```

Figure 5:
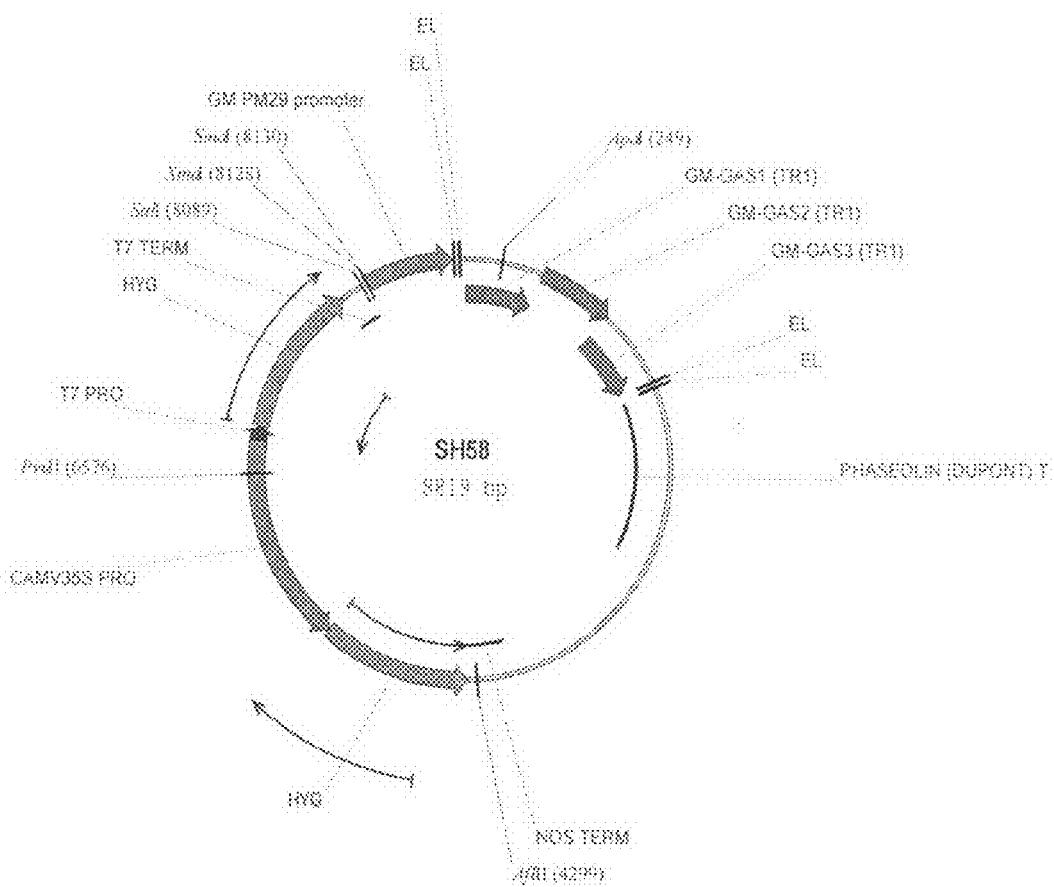
FIG. 5 is a map of plasmid SH58.
Figure 6:
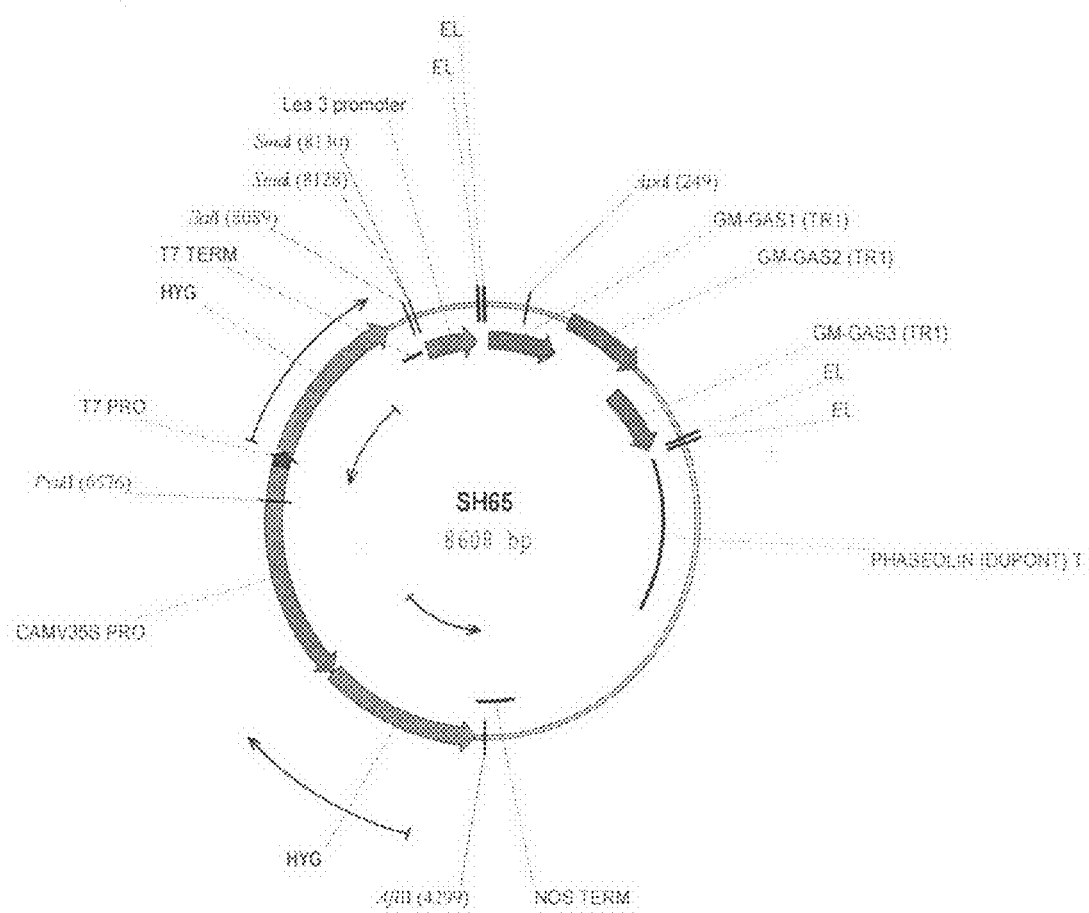
FIG. 6 is a map of plasmid SH65.

The plasmid SH56 also contains a truncated ELEL sequence (which originated during the PCR amplification of the ELEL linker) and this truncation is located at the 5' site of the Not1 sequence (SEQ ID NO:36). The nucleotide sequence of SEQ ID NO:36 is shown as follows (restriction sites listed above sequence):

Preparation of SH50, SH58 and SH65:

A Not1 fragment containing the partial sequences of soybean GAS1 (SEQ ID NO:27), GAS2 (SEQ ID NO:30) and GAS3 (SEQ ID NO:33) was digested from pJMS10 (described above) and then ligated into SH49 previously digested with Not1, creating the plasmid SH50 (SEQ ID NO:40 and FIG. 9). This plasmid revealed a potential unintentional open reading frame (FIG. 9). To eliminate this unintentional open reading frame a novel plasmid (SH58) was constructed that added a stop codon (TAA) 5' of the GAS1 polynucleotide fragment as follows. A polynucleotide fragment encoding part of the soybean galactinol synthase 1 (GAS1) (SEQ ID NO:22 which is identical to SEQ ID NO:6 of U.S. Pat. Nos. 5,773,699 and 5,648,210) was amplified by standard PCR methods using Pfu Turbo DNA polymerase (Stratagene, La Jolla, Calif.) and the following primer set. The GAS1 oligonucleotide primers were designed to add a Not1 restriction endonuclease site at the 5' end as well as a stop codon (TAA) 3' adjacent to the Not1 site, and a Xho1 site to the 3' end (SEQ ID NO:37 and SEQ ID NO:26, respectively). The DNA sequence comprising the 519 bp polynucleotide from soybean GAS1 is shown in SEQ ID NO:38. The GAS2 and GAS3 polynucleotides were prepared as described for pJMS10 (see above). A Not1 fragment containing all the partial sequences of soybean galactinol synthase 1, 2 and 3 was then ligated intoS H55 (FIG. 4) and SH56 (FIG. 3) previously digested with Not1 creating the plasmids SH58 (SEQ ID NO:41 and FIG. 5) and SH65 (FIG. 6), respectively.

Example 7

Transformation of Soybean Embryo Cultures with LEA3 and PM29 Driven Gene Silencing Vectors Soybean somatic embryos were transformed with the seed-preferred expression vectors SH50 (SEQ ID NO:40 and FIG. 9) and SH58 (SEQ ID NO:41 and FIG. 5) by the method of particle gun bombardment (Klein, T. M. et al., Nature (London) 327:70-73 (1987); U.S. Pat. No. 4,945,050, hereinafter "Klein, T. M., (1987)" ) to study the possibility of reducing Raffinose Family Oligosaccharides (RFOs).

Soybean somatic embryos from the Jack cultivar were induced as follows. Cotyledons (3 mm in length) were dissected from surface sterilized, immature seeds and were cultured for an additional 6-10 weeks in the light at 26° C. on a Murashige and Skoog media containing 7 g/L agar and supplemented with 10 mg/mL 2,4-D. Globular stage somatic embryos, which produced secondary embryos, were then excised and placed into flasks containing liquid MS medium supplemented with 2,4-D (10 mg/mL) and cultured in the light on a rotary shaker. After repeated selection for clusters of somatic embryos that multiplied as early, globular staged embryos, the soybean embryogenic suspension cultures were maintained in 35 mL liquid media on a rotary shaker, 150 rpm, at 26° C. with fluorescent lights on a 16:8 hour

```
                                                    missing "cgctcatcgtcgag"
 Eag1                                          Eag1                     ⇓
cggccg gagctggtcatctcgctcatcgtcgagtcg gcggccg gagctggtcatcttcg Not1
gcggccgc
``` day/night schedule. Cultures were subcultured every two weeks by inoculating approximately 35 mg of tissue into 35 mL of liquid medium.

Soybean embryogenic suspension cultures were then transformed by the method of particle gun bombardment (Klein, T. M., (1987)), using a DuPont Biolistic™ PDS1000/HE instrument (helium retrofit). To 50 µL of a 60 mg/µL 1 mm gold particle suspension were added (in order): 5 µL of 1 mg/µL DNA (pSH50 or pSH58), 20 µL of 0.1 M spermidine, and 50 µL of 2.5 M CaCl$_2$. The particle preparation was then agitated for three minutes, spun in a microfuge for 10 seconds and the supernatant removed. The DNA-coated particles were then washed once in 400 µL 70% ethanol and resuspended in 40 µL of anhydrous ethanol. The DNA/particle suspension was sonicated three times for one second each. Five µL of the DNA-coated gold particles was then loaded on each macro carrier disk.

Approximately 300-400 mg of a two-week-old suspension culture was placed in an empty 60×15-mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded three times. Following bombardment, the tissue was divided in half and placed back into liquid and cultured as described above.

Five to seven days post bombardment, the liquid media was exchanged with fresh media, and eleven to twelve days post bombardment with fresh media containing 50 mg/mL hygromycin. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each new line was treated as an independent transformation event. These suspensions were then subcultured and maintained as clusters of immature embryos.

These immature soybean embryos were dried-down (by transferring them into an empty small petridish that was seated on top of a 10 cm petridish containing some agar gel to allow slow dry down) to mimic the last stages of soybean seed development. Dried-down embryos are capable of producing plants when transferred to soil or soil-less media. Storage products produced by embryos at this stage are similar in composition to storage products produced by zygotic embryos at a similar stage of development and most importantly the storage product profile is predictive of plants derived from a somatic embryo line (PCT Publication No. WO 94/11516, which published on May 26, 1994).

Example 8

Raffinose Family Oligosaccharide (RFO) Analysis of PM29 Driven Transgenic Soybean Somatic Embryos Raffinose Family Oligosaccharides (galactinol, raffinose, stachyose, etc.) of transgenic somatic embryos identified in Example 7 and containing the PM29 promoter driven recombinant expression construct described in Example 6 was measured by thin layer chromatography. Somatic embryos were extracted with hexane then dried. The dried material was resuspended in 80% methanol, incubated at room temperature for 1-2 hours, centrifuged, and 2 microliters of the supernatant is spotted onto a TLC plate (Kieselgel 60 CF, from EM Scientific, Gibbstown, N.J.; Catalog No. 13749-6). The TLC was run in ethylacetate:isopropanol:20% acetic acid (3:4:4) for 1-1.5 hours. The air dried plates were sprayed with 2% sulfuric acid and heated until the charred sugars were detected. As shown in FIG. 7 the two lines labeled PM29-GAS show reduced levels of raffinose sugars (raffinose and stachyose lowest bands) when compared to a to wild-type soybean. The arrow indicates somatic embryos with reduced raffinose family oligosaccharides. (WT=wild type control, S=sucrose, Rf=raffinose and St=stachyose standard)

What is claimed is:

1. A recombinant expression construct comprising a promoter and a heterologous nucleic acid fragment operably linked to said promoter, wherein said promoter controls seed-specific expression of said heterologous nucleic acid fragment in a host cell, and wherein said promoter comprises SEQ ID NO: 2.

2. A cell comprising in its genome the recombinant expression construct of claim 1.

3. A seed comprising in its genome the recombinant expression construct of claim 1.

4. A plant comprising in its genome the recombinant expression construct of claim 1.

5. The plant of claim 4 wherein said plant is a dicotyledonous plant.

6. The recombinant expression construct of claim 1 wherein the heterologous nucleic acid fragment encodes a galactinol synthase.

7. A plant stably transformed with a recombinant expression construct comprising a soybean promoter and a heterologous nucleic acid fragment operably linked to said promoter, wherein said promoter controls seed-specific expression of said heterologous nucleic acid fragment in a plant cell, and wherein said promoter comprises SEQ ID NO: 2.

* * * * *

UNITED STATES PATENT AND TRADEMARK OFFICE
CERTIFICATE OF CORRECTION

PATENT NO. : 7,291,765 B2
APPLICATION NO. : 11/622573
DATED : November 6, 2007
INVENTOR(S) : Zhan-Bin Liu and Johan M. Stoop It is certified that error appears in the above-identified patent and that said Letters Patent is hereby corrected as shown below:

In the Claims
Column 62, Line 3 please insert claim 6 as follows -- 6. The plant of claim 5 wherein the plant is soybean. --.

Column 62, Line 6-12 please renumber the following "6. The recombinant expression construct of claim 1 wherein the heterologous nucleic acid fragment encodes a galactinol synthase." to read as -- 7. The recombinant expression construct of claim 1 wherein the heterologous nucleic acid fragment encodes a galactinol synthase. --.

Column 62, Line 12-16 please renumber the following "7. A plant stably transformed with a recombinant expression construct comprising a soybean promoter and a heterologous nucleic acid fragment operably linked to said promoter, wherein said promoter controls seed-specific expression of said heterologous nucleic acid fragment in a plant cell, and wherein said promoter comprises SEQ ID NO: 2." to read as -- 8. A plant stably transformed with a recombinant expression construct comprising a soybean promoter and a heterologous nucleic acid fragment operably linked to said promoter, wherein said promoter controls seed-specific expression of said heterologous nucleic acid fragment in a plant cell, and wherein said promoter comprises SEQ ID NO: 2. --.

Signed and Sealed this

Thirty-first Day of March, 2009

JOHN DOLL
*Acting Director of the United States Patent and Trademark Office*